United States Patent
Burdge et al.

(10) Patent No.: US 11,204,120 B2
(45) Date of Patent: Dec. 21, 2021

(54) FLUID HANDLING COMPONENTS

(71) Applicant: Colder Products Company, St. Paul, MN (US)

(72) Inventors: David A. Burdge, Richfield, MN (US); Charles W. Extrand, Minneapolis, MN (US); Koray Sekeroglu, Eden Prairie, MN (US)

(73) Assignee: Colder Products Company, Roseville, MN (US)

( * ) Notice: Subject to any disclaimer, the term of this patent is extended or adjusted under 35 U.S.C. 154(b) by 0 days.

(21) Appl. No.: 16/646,813

(22) PCT Filed: Sep. 13, 2018

(86) PCT No.: PCT/US2018/050833
§ 371 (c)(1),
(2) Date: Mar. 12, 2020

(87) PCT Pub. No.: WO2019/055621
PCT Pub. Date: Mar. 21, 2019

(65) Prior Publication Data
US 2020/0300396 A1    Sep. 24, 2020

Related U.S. Application Data

(60) Provisional application No. 62/558,210, filed on Sep. 13, 2017.

(51) Int. Cl.
*F16L 37/40* (2006.01)
*F16L 37/42* (2006.01)
*F16L 37/084* (2006.01)

(52) U.S. Cl.
CPC ............... *F16L 37/40* (2013.01); *F16L 37/42* (2013.01); *F16L 37/0841* (2013.01)

(58) Field of Classification Search
CPC . F16L 37/35; F16L 37/32; F16L 37/30; F16L 37/42; F16L 37/40; F16L 37/38; F16L 29/02; F16L 29/04
See application file for complete search history.

(56) References Cited

U.S. PATENT DOCUMENTS

| | | | | |
|---|---|---|---|---|
| 1,869,411 A | * | 8/1932 | De Mooy | F16L 37/42 137/613 |
| 2,905,485 A | * | 9/1959 | Zajac | F16L 37/22 251/149.6 |

(Continued)

OTHER PUBLICATIONS

International Search Report and Written Opinion in PCT Appln. No. PCT/US2018/050833, dated Dec. 11, 2018, 15 pages.

(Continued)

*Primary Examiner* — David Colon-Morales
(74) *Attorney, Agent, or Firm* — Fish & Richardson P.C.

(57) ABSTRACT

This document describes devices and methods for reducing liquid spillage, such as fluid coupling devices that include one or more apertures that reduce spillage when the fluid coupling devices are disconnected. In some embodiments, the one or more apertures are designed with features to increase a level of acceleration that liquid within an internal volume of the fluid coupling devices would need to be exposed to in order to spill from the internal volume via the one or more apertures.

8 Claims, 20 Drawing Sheets

(56) References Cited

U.S. PATENT DOCUMENTS

| | | | | |
|---|---|---|---|---|
| 3,052,261 | A * | 9/1962 | Nyberg | A62C 33/00 |
| | | | | 137/614.05 |
| 3,177,018 | A * | 4/1965 | Goodwin | F16L 37/40 |
| | | | | 285/277 |
| 3,566,918 | A * | 3/1971 | Rauen | F16L 37/42 |
| | | | | 137/614.04 |
| 3,567,175 | A * | 3/1971 | Sciuto, Jr. | F16L 37/23 |
| | | | | 251/149.6 |
| 4,541,457 | A * | 9/1985 | Blenkush | F16L 37/0841 |
| | | | | 137/614.05 |
| 4,612,953 | A | 9/1986 | Caroll et al. | |
| 4,863,201 | A * | 9/1989 | Carstens | F16L 37/0841 |
| | | | | 285/317 |
| 4,962,881 | A * | 10/1990 | Otsuki | F16L 37/40 |
| | | | | 251/149.7 |
| 5,215,113 | A * | 6/1993 | Terry | F16K 17/30 |
| | | | | 137/460 |
| 5,293,902 | A * | 3/1994 | Lapierie | B60H 1/00585 |
| | | | | 137/614.04 |
| 5,485,982 | A * | 1/1996 | Gunderson | F16L 37/42 |
| | | | | 251/149.6 |
| 5,494,074 | A | 2/1996 | Ramacier, Jr. et al. | |
| 5,607,139 | A * | 3/1997 | Kjellberg | F16L 37/42 |
| | | | | 251/149.6 |
| 5,845,943 | A * | 12/1998 | Ramacier, Jr. | F16L 37/42 |
| | | | | 285/12 |
| 6,283,443 | B1 * | 9/2001 | Taneya | F16L 37/133 |
| | | | | 251/149.6 |
| 6,557,904 | B2 * | 5/2003 | Naito | F16L 29/02 |
| | | | | 251/149.6 |
| 6,814,341 | B2 * | 11/2004 | Lacroix | F16L 37/0841 |
| | | | | 251/149.1 |
| 6,890,004 | B2 * | 5/2005 | Naito | F16L 37/22 |
| | | | | 285/314 |
| 6,920,895 | B2 * | 7/2005 | Avis | F16K 17/30 |
| | | | | 137/462 |
| 7,472,930 | B2 * | 1/2009 | Tiberghien | F16L 37/0841 |
| | | | | 285/316 |
| 8,356,794 | B1 * | 1/2013 | Liu | F16L 37/23 |
| | | | | 251/149.9 |
| 8,641,013 | B2 * | 2/2014 | Liu | F16L 37/42 |
| | | | | 251/149.9 |
| 9,279,530 | B2 * | 3/2016 | Schmidt | F16L 37/28 |
| 9,506,590 | B2 * | 11/2016 | Wilhelm | F16L 37/413 |
| 9,739,367 | B2 * | 8/2017 | Kujawski, Jr. | F16H 61/0009 |
| 10,221,950 | B1 * | 3/2019 | Stearns | F16L 37/40 |
| 10,514,121 | B2 * | 12/2019 | Wada | F16L 37/32 |
| 10,975,982 | B2 * | 4/2021 | Wilhelm | F16D 39/00 |
| 2005/0101939 | A1 | 5/2005 | Mitchell | A61M 39/1011 |
| | | | | 604/533 |
| 2007/0065637 | A1 * | 3/2007 | Extrand | B82Y 30/00 |
| | | | | 428/141 |
| 2011/0101675 | A1 * | 5/2011 | Smith, III | E21B 33/038 |
| | | | | 285/119 |
| 2013/0333767 | A1 | 12/2013 | Schmidt | |
| 2014/0116533 | A1 * | 5/2014 | Edler | F16L 37/42 |
| | | | | 137/315.01 |
| 2016/0238173 | A1 | 8/2016 | Kujawki, Jr. et al. | |

OTHER PUBLICATIONS

International Preliminary Report on Patentability in PCT Appln. No. PCT/US2018/050833, dated Mar. 17, 2020, 15 pages.

* cited by examiner

//<br>
FLUID HANDLING COMPONENTS

CROSS-REFERENCE TO RELATED APPLICATIONS

This application is a National Stage application under 35 U.S.C. § 371 of International Application No. PCT/US2018/050833, having an International Filing Date of Sep. 13, 2018, which claims priority to U.S. Application Ser. No. 62/558,210, filed on Sep. 13, 2017. The disclosure of the prior application is considered part of the disclosure of this application, and is incorporated in its entirety into this application.

TECHNICAL FIELD

This document describes devices and methods for reducing fluid spillage, and in some embodiments, fluid handling components such as coupling devices including a valve assembly that reduces spillage when disconnected.

BACKGROUND

Fluid handling components that allow fluid communication between two or more components are well known. Fluid couplings often include features that allow male and female components to be quickly connected or disconnected, and may include one or more internal valve components that selectively block or allow flow of fluid through the coupling. While various fluid couplings may allow selective closure to stop flow, for example when the coupling is disconnected, some residual fluid present in a coupling housing may spill from a disconnected end of the coupling.

SUMMARY

In some embodiments, fluid handling devices and methods are provided that are configured to reduce the potential for spillage from an open end of a fluid handling component. For example, some fluid coupling devices described herein may reduce spillage of fluid present in an internal volume of the coupling device after disconnection from a use with a mating device. Fluid present in such an internal volume (e.g., between a seal and one or more apertures) may be prevented from escaping through the fluid coupling component apertures and an open end of the fluid coupling component. In this way, material loss, soiling and costs associated with spillage may be reduced. Additionally, the potential for air to enter the internal volume to replace the spillage may be advantageously reduced.

In some embodiments, a fluid coupling device is described including one or more apertures, a sealing surface, and an internal volume between the aperture(s) and the sealing surface. The aperture(s) can have a size, shape and configuration that readily allows fluid to flow through the fluid coupling device when in a connected configuration, while reducing spillage of fluid out of an open end of the fluid coupling device when in a disconnected configuration. While examples are provided using the context of fluid coupling devices, it should be understood that the anti-spillage concepts described herein can be implemented in other fluid handling component contexts such as, but not limited to, dip tubes, drop tubes, nipples, nozzles, tubes, pipes, valves, fittings, and the like.

In one aspect, this disclosure is directed to an anti-spillage poppet valve assembly that includes a first coupling body member configured to mate with a second coupling body member and a first valve assembly. The first coupling body member defines a longitudinal axis and an interior space defined by an inner sidewall between a first port and a second port. The interior space has an interior diameter ($D_{body}$) and a cross-sectional area ($A_{body}$) measured orthogonally to the longitudinal axis. The first valve assembly is disposed within the interior space. The first valve assembly includes a first closure member having a forward end region, a rear end region, a piston head proximate the forward end region and a sealing surface proximate the rear end region and spaced from the piston head. The first valve assembly also includes a piston head having one or more apertures extending longitudinally therethrough. The one or more apertures define a total open cross-sectional area ($A_{apertures}$). Each aperture has a maximum major dimension ($d_{aperture}$). The maximum major dimension ($d_{aperture}$) is a maximum dimension between distant sides of each of the one or more apertures. The first valve assembly also includes an internal volume defined by the interior space of the first coupling body member between the piston head and the sealing surface. The first closure member is longitudinally movable between a closed position in which the sealing surface prevents fluid communication between the first port and the second port, and an open position in which the first port and the second port are in fluid communication. Wherein $0.2*(d_{critical}) < (d_{aperture}) < 1.0*(d_{critical})$. ($d_{critical}$) is determined according to the formula:

$$d_{critical} = \left[(3+\cos\theta_r)\left\{3+\cos\theta_r+\left[\frac{1}{4}-\left(\frac{1}{2}-\frac{1}{3+\cos\theta_r}\right)^2\right]^{-1/2}\right\}\frac{\gamma}{\rho g}\right]^{1/2}$$

where $\gamma$ is the surface tension of a fluid in the first coupling body member in N/m, $\rho$ is the density of the fluid in kg/m$^3$, $\theta_r$ is a receding angle defined between the fluid and a side of one of the apertures, and g is a gravity constant of 9.81 m/s$^2$.

In another aspect, this disclosure is directed to an anti-spillage poppet valve assembly. The anti-spillage poppet valve assembly includes (i) a male coupling body member defining a longitudinal axis and a male interior space defined by an inner sidewall between a first end and a second end; (ii) a female coupling body member defining a longitudinal axis and a female interior space defined by an inner sidewall between a first port and a second port, the interior space having an interior diameter ($D_{body}$) between 6 mm and 72 mm and a cross-sectional area ($A_{body}$) measured orthogonally to the longitudinal axis; and (iii) a valve assembly disposed within the female body interior space. The valve assembly includes (a) a first closure member having a forward end region, a rear end region, a piston head proximate the forward end region and a sealing surface proximate the rear end region and spaced from the piston head, the piston head having one or more apertures extending longitudinally therethrough, the one or more apertures defining a total open cross-sectional area ($A_{apertures}$), and each having a maximum major dimension ($d_{aperture}$), the maximum major dimension ($d_{aperture}$) being a maximum dimension between distant sides of each the apertures, and (b) a first internal volume defined by the interior space of the female coupling body member between the piston head and the sealing surface. The first closure member is longitudinally movable between a closed position in which the sealing surface prevents fluid communication between the first port and the second port, and an open position in which the first port and the second port are in fluid communication. Wherein 2 mm<($d_{aperture}$)<5 mm, and 0.4*($A_{body}$)< ($A_{apertures}$)<0.9*($A_{body}$).

In another aspect, this disclosure is directed to an anti-spillage device. The anti-spillage device includes a fluid body member defining a longitudinal axis and an interior space defined by an inner sidewall between a first end and a second end. The interior space has an interior diameter ($D_{body}$) and a cross-sectional area ($A_{body}$) measured orthogonally to the longitudinal axis. The fluid body member comprises one or more apertures defining a total open cross-sectional area ($A_{apertures}$), and each having a maximum major dimension ($d_{aperture}$) sized to prevent spillage through the apertures.

In another aspect, this disclosure is directed to an anti-spillage valve assembly that includes: a first body member; a second body member configured to communicate with the first body member and defining a longitudinal axis and an interior space defined by an inner sidewall; means for connecting the first and second body members to provide fluid communication between the first and second body members; and means for retaining fluid in the second body member when disconnected from the first body member.

In another aspect, this disclosure is directed to a method of using an anti-spillage device. The method includes: coupling a first coupling body member to a second coupling body member, the first coupling body member defining a longitudinal axis and an interior space defined by an inner sidewall, the first coupling body member comprising means for retaining fluid in the second coupling body member when disconnected from the first coupling body member; passing a fluid through the first and second coupling body members; and disconnecting the first and second coupling body members.

In another aspect, this disclosure is directed to an anti-spillage poppet valve fluid coupling device, comprising: (a) a first coupling body member configured to mate with a second coupling body member and defining a longitudinal axis and an interior space defined by an inner sidewall between a first port and an opposing second port; and (b) a first poppet valve assembly disposed within the interior space. The poppet valve assembly includes a first closure member having a forward end region, a rear end region, a piston head proximate the forward end region and a sealing surface proximate the rear end region. The first closure member is longitudinally movable within the interior space between a closed position in which the sealing surface prevents fluid communication between the first port and the second port, and an open position in which the first port and the second port are in fluid communication. The piston head defines one or more apertures extending longitudinally therethrough, wherein each of the one or more apertures is defined by an annular lip that projects radially inward.

In another aspect, this disclosure is directed to an anti-spillage poppet valve fluid coupling device that includes: (1) a first coupling body member configured to mate with a second coupling body member and defining a longitudinal axis and an interior space defined by an inner sidewall between a first port and an opposing second port; and (2) a first poppet valve assembly disposed within the interior space. The poppet valve assembly includes a first closure member having a forward end region, a rear end region, a piston head proximate the forward end region and a sealing surface proximate the rear end region. The first closure member is longitudinally movable within the interior space between a closed position in which the sealing surface prevents fluid communication between the first port and the second port, and an open position in which the first port and the second port are in fluid communication. The piston head defines one or more apertures extending longitudinally therethrough. Each of the one or more apertures are defined by an annular longitudinally-projecting wall portion.

Some embodiments of the devices, systems and techniques described herein may provide one or more of the following advantages. First, a coupling body member having one or more apertures as described herein may retain fluid within the coupling body member and reduce the likelihood of fluid escape or spillage from an open end. Second, apertures described herein may exhibit desirable fluid retention characteristics without excessive flow restriction. The apertures may have a sufficiently large size, and a total open area, that allows adequate flow through the fluid coupling, without creating excessive flow resistance, while exhibiting desirable fluid retention (spillage prevention) characteristics. Third, apertures described herein allow a coupling body member to have an internal volume of any suitable size, as may be desired to enhance valve performance, for example. The internal volume and other geometric characteristics may by selected to optimize valve performance without increasing a quantity of fluid that may spill when the coupling body member is disconnected.

The details of one or more implementations are set forth in the accompanying drawings and the description below. Other features and advantages will be apparent from the description and drawings, and from the claims.

BRIEF DESCRIPTION OF DRAWINGS

The present description is further provided with reference to the appended Figures, wherein like structure is referred to by like numerals throughout the several views, and wherein.

DETAILED DESCRIPTION OF ILLUSTRATIVE EMBODIMENTS

Figure 1A:
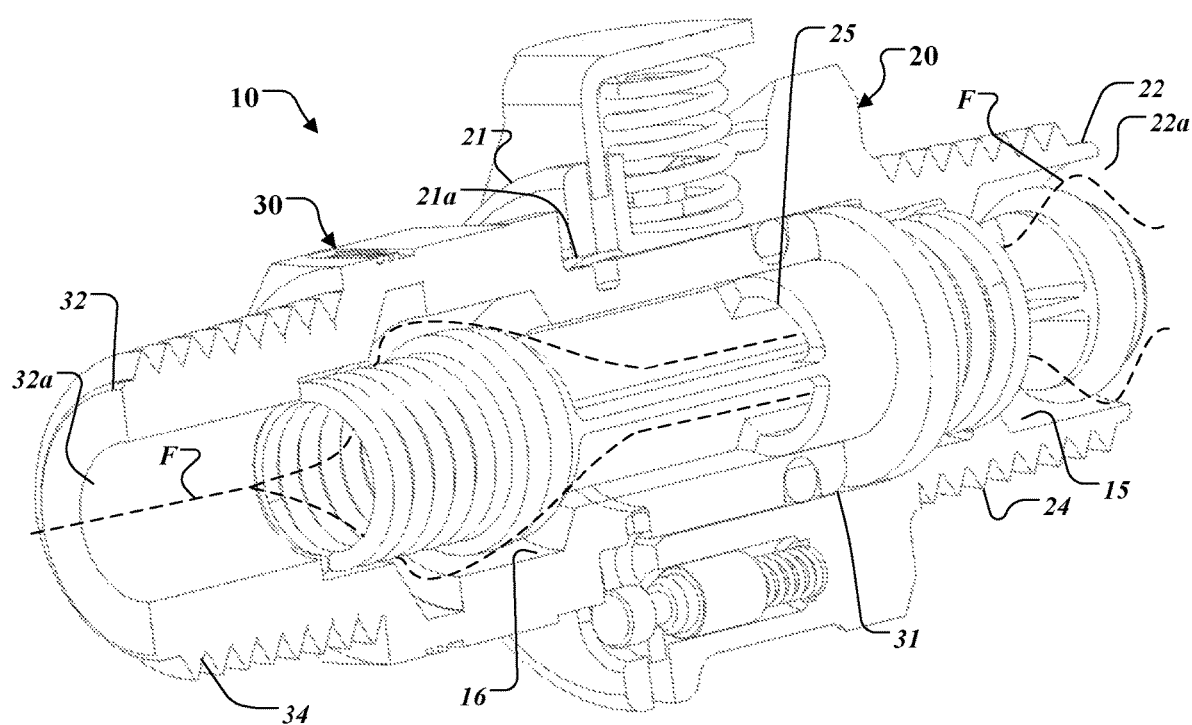
FIG. 1A shows a perspective partial cross-sectional view of exemplary first and second coupling body members in a connected configuration.
Figure 1B:
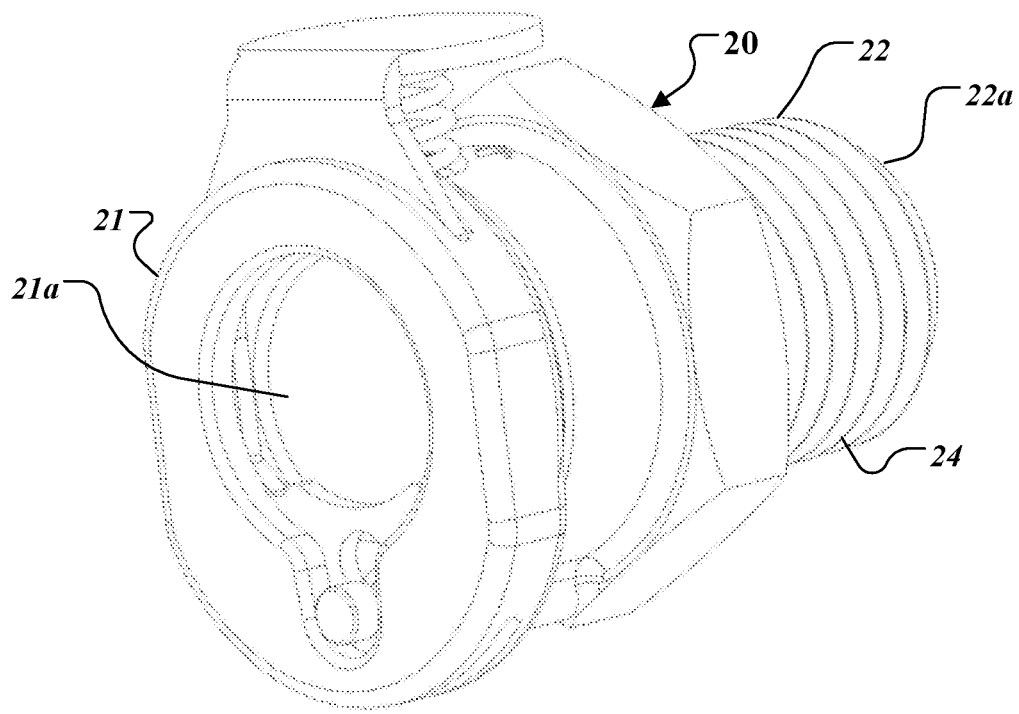
FIG. 1B shows a perspective view of an exemplary first coupling body member.
Figure 1C:
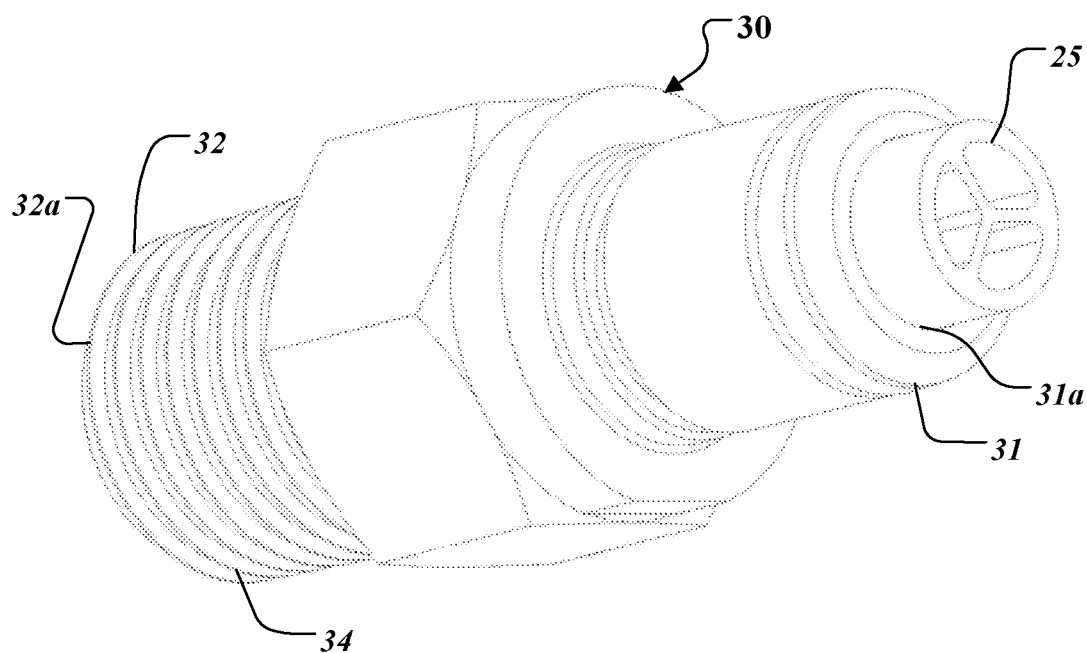
FIG. 1C shows a perspective view of an exemplary second coupling body member.

Referring to FIGS. 1A-1C, an exemplary fluid coupling device 10 is illustrated that provides fluid coupling between two fluid paths. Fluid coupling assembly 10 includes a first coupling body member 20 (FIG. 1B) and a second coupling body member 30 (FIG. 1C). First coupling body member 20 and second coupling body member 30 are connectable to provide a flow path (F) through fluid coupling assembly 10 (FIG. 1A). One or both of first and second coupling body members 20, 30 may include one or more internal apertures 25 through which fluid may flow, and one or more valve assemblies to selectively open and close a fluid passage. As described further below, the size, shape, and configuration of apertures 25 may be selected to provide desirable flow and spillage prevention characteristics of fluid coupling assembly 10, and in some embodiments, may be selected based on fluid properties of one or more fluids that fluid coupling assembly 10 is used with. While the depicted example is a fluid coupling device, it should be understood that the anti-spillage concepts described herein can be implemented in other fluid handling component contexts such as, but not limited to, dip tubes, drop tubes, nipples, nozzles, tubes, pipes, valves, fittings, and the like.

FIG. 1B shows an exemplary embodiment of a first coupling body member 20 including a female body having a first end 21 and a second end 22. A first port 21a is positioned at first end 21 and defines an opening that may receive at least a portion of second coupling body member 30 or other suitable component connectable with first coupling body member 20. A second port 22a is positioned at second end 22 and may be brought into fluid communication with one or more fluid sources or outlets. One or more attachment features 24 are positioned proximate second end 22 and second port 22a. In the depicted embodiment, attachment feature 24 is an externally-threaded portion configured to mate with a corresponding internally-threaded component. In various other exemplary embodiments, attachment feature 24 may include a one or more barbs, a bayonet connector, a snap-fit connector, or other type of attachment feature suitable to facilitate fluid communication with one or more components attached to first coupling body member 20 at second port 22a, such as a component of fluid dispensing equipment, hose, tube, container, valve, fitting or other connector.

FIG. 1C shows an exemplary embodiment of a second coupling body member 30 including a male body having a first end 31 and a second end 32. First end 31 defines one or more ports 31a and may be received by at least a portion of first coupling body member 20, for example, or other component connectable with second coupling body member 30. A second port 32a is positioned at second end 32 and may be brought into fluid communication with one or more fluid sources or outlets. One or more attachment features 34 are positioned proximate second end 32 and second port 32a. In the depicted embodiment, attachment feature 34 includes an externally-threaded surface attachable to a corresponding internally-threaded coupling of a fluid dispensing component, hose, tube, container, valve, fitting or another connector, for example, to allow fluid communication with second coupling body member 30. In various exemplary embodiments, attachment feature 34 may include one or more ribs or barbs configured to frictionally retain a hose or flexible component, a bayonet connector, snap-fit connector, or other attachment feature allowing fluid communication with one or more components attached to second coupling body member 30 at second port 32a.

In use, first end 31 of second coupling body member 30 may be received by first port 21a of first coupling body member 20 such that first and second coupling body members 20, 30 may be sealingly joined, as shown in FIG. 1A. Inner sidewalls 15, 16 of first and second coupling body members 20, 30 define a flow passage (F) from second end port 22a of first coupling body member 20, through first end ports 21a, 31, and out second end port 32a for second coupling body member 30. Flow characteristics through fluid coupling device 10, and resistance to leakage of fluid that may be present in first and/or second coupling body members 20, 30, may be effected by the geometry and configuration of apertures 25 within fluid coupling assembly 10 that define at least a portion of flow passage (F), as described further herein.

Figure 2A:
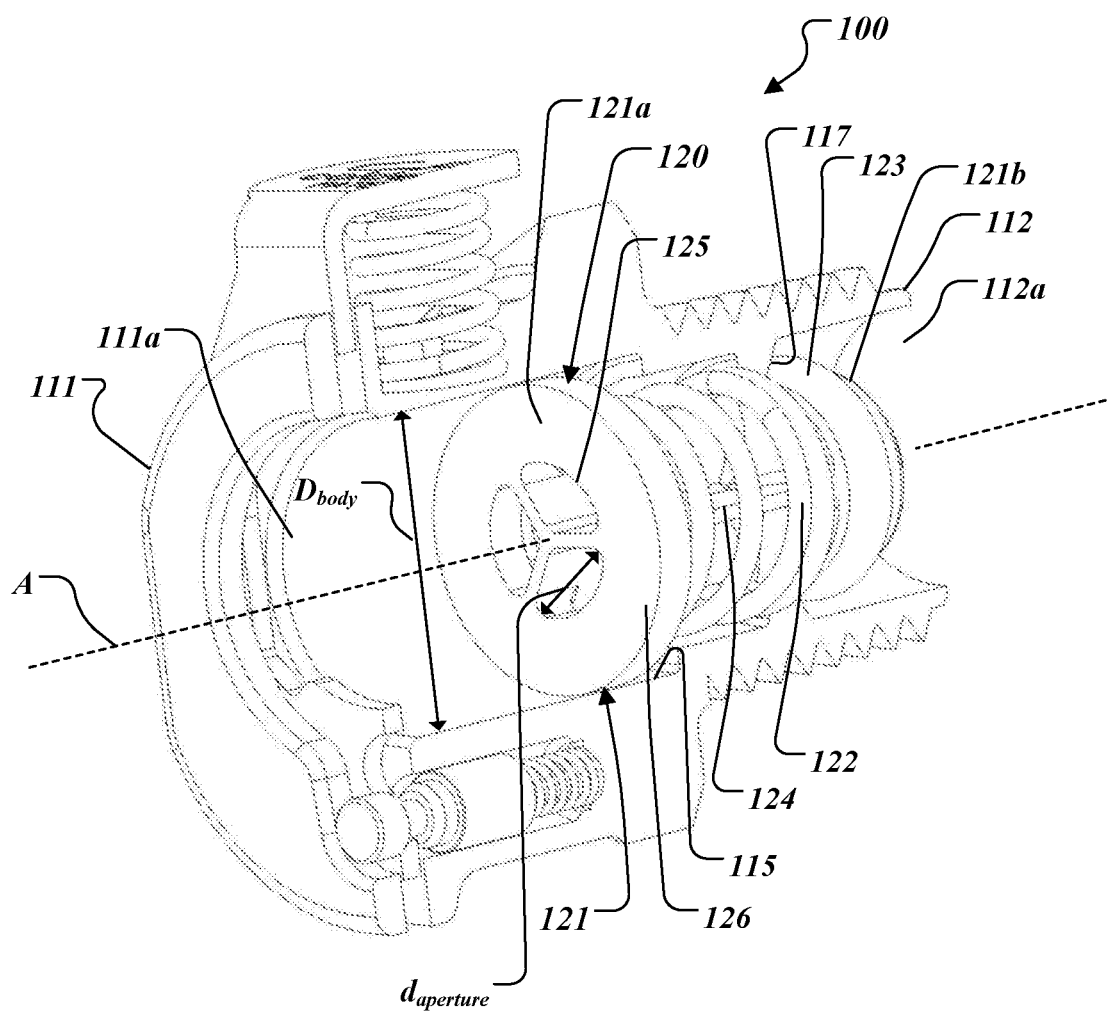
FIG. 2A shows a perspective partial cross-sectional view of an exemplary coupling body member having a female first end.

Referring to FIG. 2A, a perspective longitudinal cross-sectional view of an exemplary coupling body member 100 is shown. Coupling body member 100 includes a longitudinal axis A and an interior space defined by inner sidewall 115 between first and second ends 111, 112. First and second ends 111, 112 define first and second ports 111a, 112a, respectively, connectable to another coupling body member, for example, or other component for receiving or delivering a flow of fluid, and may include female, male, or other suitable connecting features. Interior space has an interior diameter ($D_{body}$) defined between opposing wall portions of inner sidewall 115, and a cross-sectional area ($A_{body}$) measured orthogonally to longitudinal axis A. The interior space defines a passage that fluid may flow through between first and second ports 111a, 112a of coupling body member 100.

In an exemplary embodiment, a first valve assembly 120 is disposed within the interior space and is configured to be moveable between an open position and a closed position to selectively allow fluid flow through coupling body member 100. First valve assembly 120 includes a first closure member 121, a biasing member 122, and a seal 123. First closure member 121 includes a forward end 121a, a rear end 121b, and an elongate portion 124 extending between forward and rear ends 121a, 121b. In an exemplary embodiment, a piston head 126 is positioned proximate forward end 121a and defines valve apertures 125 extending longitudinally through a thickness of piston head 126. Apertures 125 allow fluid to flow through piston head 126 when first valve assembly 120 is in an open configuration and may have a particular size, shape and configuration to provide desirable flow and fluid retention characteristics. Seal 123 is positioned proximate rear end 121b and spaced from piston head 126. In an exemplary embodiment, rear end 121b is a solid end without openings or passages extending through, such that fluid may only flow through coupling body member 100 by passing between rear end 121b and inner sidewall 115 when first valve assembly 120 is in an open configuration.

In an exemplary embodiment, biasing member 122 (e.g., a compression spring) biases first closure member 121 towards a closed position in which seal 123 of first valve assembly 120 contacts a portion of inner sidewall 115. For example, inner sidewall 115 may include a flange or valve seat 117 that seal 123 may sealingly engage to prevent fluid flow between first closure member 121 and inner sidewall 115. Biasing member 122 may be a coil spring that partially surrounds elongate portion 122 of first closure member 121. In various other exemplary embodiments, biasing member 122 may be a cantilever spring, compression mechanism, or another biasing member configured to bias first closure member 121 towards a closed position. Seal 123 may be provided by any suitable surface brought into sealing engagement with a portion of inner sidewall 115 or other component of coupling body member 100. In an exemplary embodiment, seal 123 is an elastomeric gasket (e.g., an o-ring) positioned proximate rear end 121b and made from a different material than piston head 126. The elastomeric gasket may be mechanically maintained in a groove of first closure member 120 configured to receive the elastomeric gasket, for example.

First valve assembly 120 may be operated between open and closed positions by longitudinal movement of first closure member 121 along axis A, for example. In an exemplary embodiment, first closure member 121 is slidable within the interior space of coupling body member 100 and is biased towards a closed position by biasing member 122. When first port 111a of coupling body member 100 is connected to a suitable component, such as another coupling body member, contact between one or more components during connection exerts a force on piston head 126 or other component of first valve assembly 120 such that first closure member 121 moves towards an open position. Closure member 121 may move towards second end 112a, for example, as it moves to an open position, compressing biasing member 122. Seal 123 becomes separated from inner surface 115 so that a path for fluid flow is opened between rear end region 121b of first closure member 121 and inner surface 115 of coupling body member 100. When coupling body member 100 is disconnected, biasing member 122 urges first closure member 121 back to a closed configuration. Alternatively or additionally, first valve assembly 120 may be manually operated between open and closed positions, for example by manually moving first closure member 121 from a closed position to an open position after coupling body member 100 is connected.

Figure 2B:
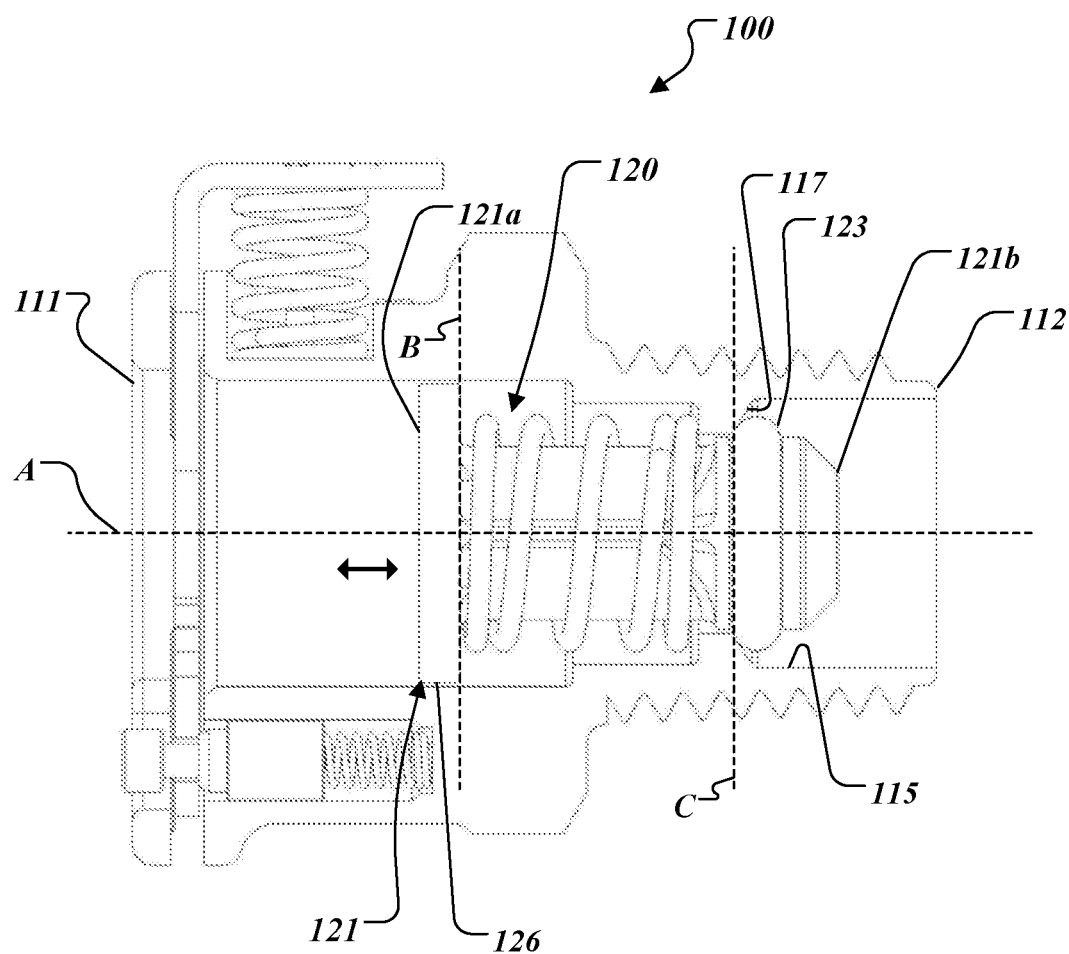
FIG. 2B shows a partial cross-sectional view of the exemplary coupling body member of FIG. 2A.

In some exemplary embodiments, some of the fluid that was flowing through coupling body member 100 may remain in an internal volume ($V_{internal}$) of coupling body member 100 after first valve assembly 120 is moved from an open configuration (in which fluid flows through coupling body member 100) to a closed configuration. For example, an internal volume ($V_{internal}$) may be defined by one or more components of coupling body member 100 through which fluid may flow, and in which fluid may be present immediately after first valve assembly 120 is moved to a closed position. In an exemplary embodiment, internal volume ($V_{internal}$) is defined by inner surface 115 of coupling body member 100 between apertures 125 of piston head 126 and seal 123 when first valve assembly 120 is in a closed position. In some embodiments, internal volume ($V_{internal}$) may thus be a volume between reference planes (B) and (C), for example, passing through coupling body member 100 orthogonal to longitudinal axis (A) (FIG. 2B). Accordingly, in some exemplary embodiments, a magnitude of internal volume ($V_{internal}$) is based at least in part on a distance between apertures 125 of piston head 126 and seal 123, and the interior diameter ($D_{body}$) of coupling body member 100.

The geometry and configuration of coupling body member 100 and first valve assembly 120 may be selected such that a fluid present in internal volume ($V_{internal}$) is retained in coupling body member 100, rather than spilling or leaking, when first end 111 is disconnected. As described further below, the present inventors have found that apertures 125 having a relatively large size as compared to other portions of coupling body member 100, such as an inner diameter ($D_{body}$) or cross-sectional area ($A_{body}$), for example, may prevent fluid in internal volume ($V_{internal}$) from escaping through apertures 125 and out of open first end 111 when valve assembly is in a closed configuration. Apertures having a relatively large size may also allow desirable flow characteristics (e.g., a low pressure drop) when coupling body member 100 is in a connected configuration, as described further herein.

In some exemplary embodiments, apertures 125 may be characterized by a maximum major dimension ($d_{aperture}$) between distant sides of each of apertures 125. In the exemplary embodiment of FIG. 2A, apertures 125 have a generally triangular or honeycomb configuration, and maximum major dimension ($d_{aperture}$) is a maximum dimension across one of apertures 125. In other exemplary embodiments, maximum major dimension ($d_{aperture}$) may be the diameter of an aperture having a circular shape, a major diameter of an aperture having an elliptical shape, or other maximum distance between distant sides of an aperture having a different shape. In some exemplary embodiments, the maximum major dimension ($d_{aperture}$) of each of apertures 125 in a particular forward end 121a is the same, and each of apertures 125 may exhibit an identical shape. In various other exemplary embodiments, the maximum major dimension ($d_{aperture}$) of two or more of apertures 125 in a particular forward end 121a may differ.

Figure 10:
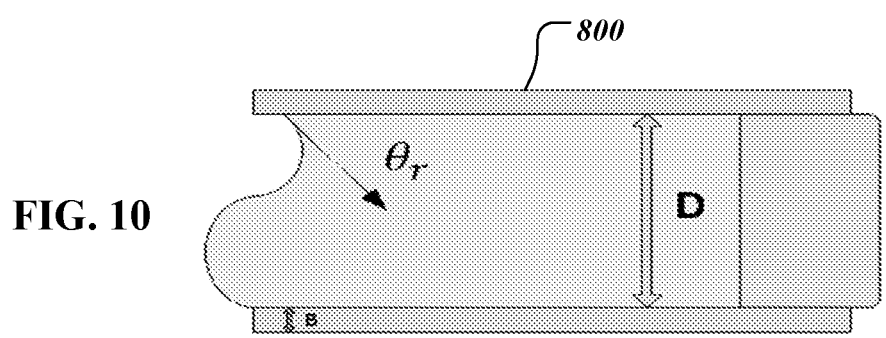
FIG. 10 schematically depicts a longitudinal cross section of a liquid-filled tube with a single open end that is undergoing a longitudinally-directed acceleration.
Figure 11:
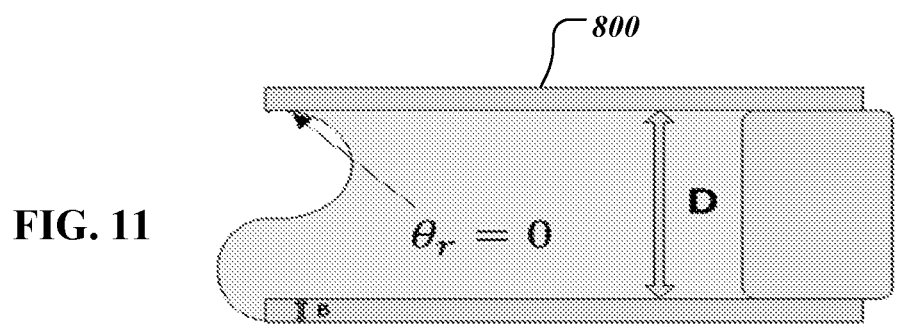
FIG. 11 schematically depicts a longitudinal cross section of another liquid-filled tube with a single open end that is undergoing a longitudinally-directed acceleration.
Figure 12:
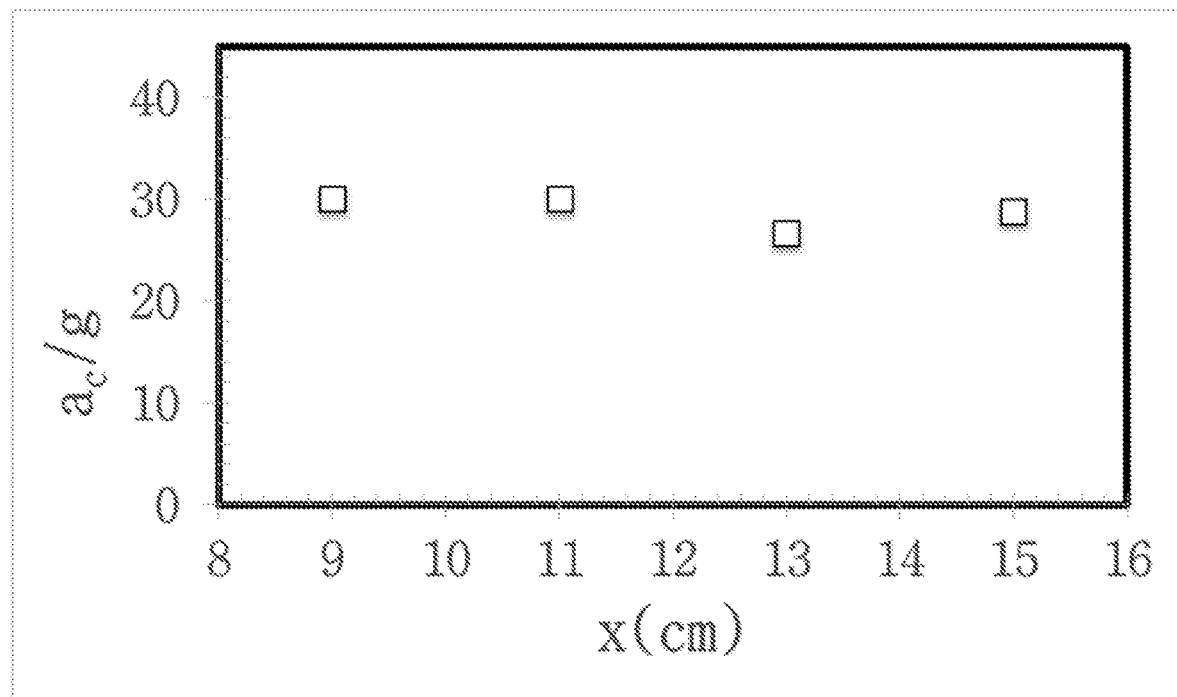
FIG. 12 is a graph of the critical accelerations (when liquid spillage occurred) measured at various positions along the length of the rotary test device of FIG. 9.

In some exemplary embodiments, the size, shape and configuration of apertures 125 may be selected based at least in part on properties of a fluid passing through coupling body member 100, in order to reduce spillage of fluid from internal volume ($V_{internal}$) through an open first end 111a of female coupling body member 100. The present inventors have found that, one factor pertaining to how a fluid may be retained in the internal volume ($V_{internal}$) of coupling body member 100, is by designing the one or more apertures 125 to have a maximum major dimension ($d_{aperture}$) that is less than a critical dimension ($d_{critical}$) determined based on surface tension and density properties of a fluid within coupling body member 100. In an exemplary embodiment, assuming the coupling body member 100 is exposed to a constant acceleration due to gravity (1 g, with no other accelerations due to impacts, jolts, etc.), a critical dimension ($d_{critical}$ or simply $d_c$) may be estimated according to Equation 1:

$$d_c = \left[ (3 + \cos\theta_r)\left\{3 + \cos\theta_r + \left[\frac{1}{4} - \left(\frac{1}{2} - \frac{1}{3 + \cos\theta_r}\right)^2\right]^{-1/2}\right\} \frac{\gamma}{\rho g} \right]^{1/2} \quad \text{(Equation 1)}$$

where $\gamma$ is the surface tension in N/m of a fluid that may flow through coupling body member 100, $\theta_r$ is the receding contact angle (the angle defined between the fluid surface and the tube wall where the fluid is deflecting inwards towards the tube, e.g., see FIGS. 10 and 11), $\rho$ is the density in kg/m³ of the fluid, and g is a gravitational constant of 9.81 m/s². That is, in an exemplary embodiment, a size of respective apertures 125 may be selected based on both surface tension and density of a fluid. Equation 1 applies, for example, for filled liquid tubes with an open bottom end that are pulled vertically from a reservoir. If the opening on the bottom of the tubes is sufficiently small (less than $d_{critical}$) liquid will be retained in the tube (without drainage). Otherwise, if the opening is sufficiently large (greater than $d_{critical}$), liquid will drain from the tubes, from the bottom up.

While the coupling body member 100 is exposed to a constant 1 g (without jolts, impacts, and the like), apertures 125 having a maximum major dimension ($d_{aperture}$) less than a critical dimension ($d_{critical}$) according to Equation (1) can tend to reduce spillage of fluid present in internal volume ($V_{internal}$) when coupling body member 100 is disconnected, while having a relatively large open area that avoids excessive flow restriction. Maximum major dimension ($d_{aperture}$) of apertures 125 may be selected based on a critical dimension ($d_{critical}$) for any suitable fluid or ranges of fluids such as, for example, water, glycerol, ethylene glycol, isopropyl alcohol, perfluoro ether oil, other fluids, and combinations of fluids. In an exemplary embodiment, critical dimension ($d_{critical}$) may be approximately 13.6 mm for water having a surface tension ($\gamma$) of 72 mN/m and density ($\rho$) of 998 kg/m'. In various exemplary embodiments, glycerol having a surface tension ($\gamma$) of about 63 mN/m and density ($\rho$) of 1260 kg/m³ may yield a critical dimension ($d_{critical}$) of approximately 11.5 mm, ethylene glycol having a surface tension ($\gamma$) of 48 mN/m and density ($\rho$) of 1110 kg/m' may yield a critical dimension ($d_{critical}$) of approximately 10.4 mm, isopropyl alcohol having a surface tension ($\gamma$) of 22 mN/m and density ($\rho$) of 786 kg/m' may yield a critical dimension ($d_{critical}$) of approximately 805 mm, and perfluoro ether oil having a surface tension ($\gamma$) of 17 mN/m and density ($\rho$) of 1880 kg/m³ may yield a critical dimension ($d_{critical}$) of approximately 4.8 mm.

In various exemplary embodiments, apertures 125 selectively designed to have a maximum major dimension ($d_{aperture}$) that is less than a critical dimension ($d_{critical}$) determined according to Equation (1). Apertures 125 having a maximum major dimension ($d_{aperture}$) less than a critical dimension ($d_{critical}$) may promote robust fluid retention characteristics when the coupling body member 100 is not subjected to sudden accelerations which may result from decoupling, dropping, impacts, and the like. In various exemplary embodiments, maximum major dimension ($d_{aperture}$) is between 30% and 100%, 35% and 95%, 40% and 90%, 45% and 85%, or about 50% of critical dimension ($d_{critical}$). Such values of maximum major dimension ($d_{aperture}$) of apertures 125 may result in desirable fluid retention characteristics for a range of fluids, while being sufficiently large to avoid excessive restriction to flow.

In an exemplary embodiment, apertures 125 have a size related to one or more components of coupling body member 100. Apertures 125 having a maximum major dimension ($d_{aperture}$) within a range of relatively large sizes as compared to one or more other components of coupling body member 100 have been found to provide a combination of desirable flow characteristics while inhibiting the potential for, or preventing, fluid spillage when disconnected. For example, apertures 125 may have a maximum major dimension ($d_{aperture}$) and a total open area ($A_{apertures}$) related to interior diameter ($D_{body}$) and/or cross-sectional area ($A_{body}$). In various exemplary embodiments, interior diameter ($D_{body}$) of coupling body member 100 is between 4 mm and 72 mm, 5 mm and 60 mm, 6 mm and 54 mm, 7 mm and 36 mm, 8 mm and 24 mm, or about 8 mm, and cross-sectional area ($A_{body}$) is between 12 mm² and 4000 mm², 19 mm² and 2900 mm², 28 mm² and 2460 mm², 38 mm² and 1100 mm², 50 mm² and 460 mm², or about 50 mm². Apertures 125 may have a total open area ($A_{apertures}$) between 40% and 95%, 45% and 90%, 50% and 85%, 55% and 80% or about 60% of cross-sectional area ($A_{body}$) of an interior space of coupling body member 100. Such values prevent excessive flow restriction by providing a flow path through apertures 125 that is similarly sized to the cross-section area ($A_{body}$) of an interior space and, in some embodiments, relatively close to a theoretical minimum flow resistance provided by cross-sectional area ($A_{body}$). Similarly, maximum major dimension ($d_{aperture}$) of apertures 125 may be relatively large as compared to an inner diameter ($D_{body}$) of coupling body member 100, for example at the location proximate forward end 121a of closure member 121. In various exemplary embodiments, maximum major dimension ($d_{aperture}$) may be between 10% and 90%, 15% and 85%, 20% and 80%, 25% and 75% or about 30% of inner diameter ($D_{body}$). Furthermore, in some exemplary embodiments in which only one, two or a small number of apertures 125 are present, maximum major dimension ($d_{aperture}$) may be relatively small compared to inner diameter ($D_{body}$). For example, in some embodiments having only a single aperture 125, maximum aperture dimension ($d_{aperture}$) is between 20% and 75%, 25% and 70%, 30% and 65%, or about 30% of inner diameter ($D_{body}$). A relatively greater total open area ($A_{apertures}$) and maximum aperture dimension ($d_{aperture}$) generally provide relatively less resistance to flow as compared to a relatively smaller total open cross-sectional area ($A_{apertures}$) or maximum aperture dimension ($d_{aperture}$). Such sizes thus avoid excessive flow restriction caused by small apertures, while retaining fluid in internal volume ($V_{internal}$) as described herein.

In various exemplary embodiments, apertures 125 having a maximum aperture dimension ($d_{aperture}$) and total open area ($A_{apertures}$) as described herein include two or more apertures. The presence of two or more apertures 125 allows the total open area ($A_{apertures}$) to be relatively large while maximum aperture dimension ($d_{aperture}$) remains within ranges described herein, and less than critical dimension ($d_{critical}$), for example. In an exemplary embodiment, apertures 125 including an array of three apertures 125 allows each aperture to exhibit a relatively large size while having a suitable maximum aperture diameter ($d_{aperture}$). In various exemplary embodiments, apertures 125 may include between 2 and 18, 3 and 15, 4 and 12, or 3 to 5 or more apertures 125. For example, an array of three apertures 125 may be configured to exhibit maximum aperture diameters ($d_{aperture}$) that are less than 75%, 65%, 55%, 50%, 45%, 40%, 35%, 30%, 25%, 20%, 15%, 10%, or less of inner diameter ($D_{body}$), while still providing a total open area ($A_{apertures}$) that is greater than 30%, 35%, 40%, 45%, 50%, 55%, 60%, 65%, 70%, 75%, 80%, 85%, or greater than 90% of cross-sectional area ($A_{body}$).

In various exemplary embodiments, apertures 125 provide desirable flow properties when coupling body member 100 is in an open configuration, and prevent spillage or escape of fluid from open first port 111a when coupling body member 100 is in a closed configuration, by having a maximum aperture dimension ($d_{aperture}$) between 2 mm and 9 mm, 2.5 mm and 8.5 mm, 3 mm and 8 mm, 3.5 mm and 7.5 mm, 4 mm and 7 mm, 4.5 mm and 6.5 mm, or about 5 mm. Such maximum aperture dimensions ($d_{aperture}$) of each aperture 125 may prevent dripping or spillage of particular fluids present in internal volume ($V_{internal}$) when coupling body member 100 is disconnected. Apertures 125 having a maximum major dimension ($d_{aperture}$) within such ranges may retain more than 25%, more than 50%, more than 75%, more than 85%, more than 95% or approximately 100% of fluid present in internal volume ($V_{internal}$) immediately after first end 111 of coupling body member 100 is disconnected and/or first valve assembly 120 is moved to a closed configuration.

Figure 3A:
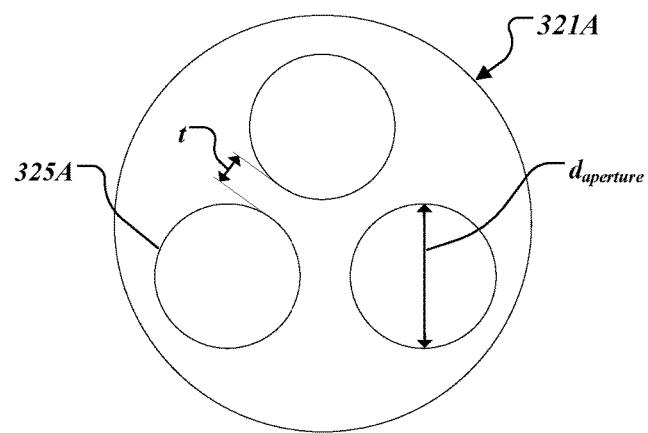
FIGS. 3A-3C show exemplary fluid coupling closure members (valves) having a plurality of valve apertures.
Figure 3B:
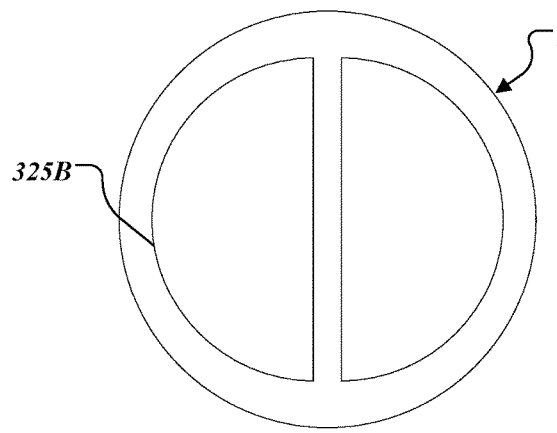
Figure 3C:
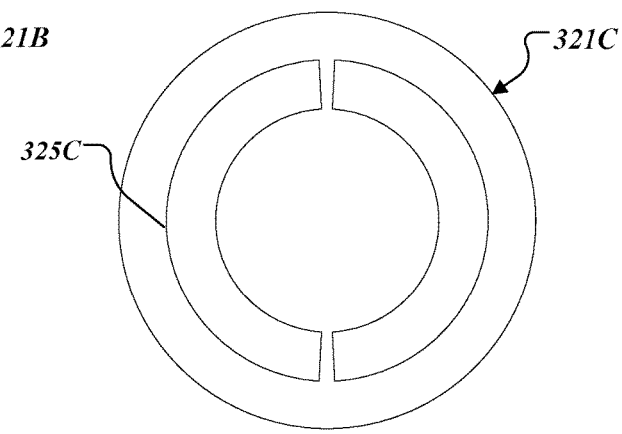

FIGS. 3A-3C show front views of exemplary closure members 321A, 321B, and 321C having apertures 325A, 325B, and 325C that provide a flow path through a forward end of a fluid coupling device. In the exemplary embodiment of FIG. 3A, closure member 321A includes three apertures 325A having a circular shape and a maximum major dimension ($d_{aperture}$) that is the diameter of each respective aperture 325A.

Apertures 325A are separated by a wall thickness (t) that provides spacing between respective apertures 325A. In some exemplary embodiments, wall thickness (t) is greater than 0.25 mm, 0.5 mm, or greater than about 0.75 mm. Such wall thicknesses (t) allows apertures 325A to prevent fluid in an internal volume from spilling or escaping as described herein, even if a total dimension across all of apertures 325A, for example between opposite outer edges of adjacent apertures 325A, exceeds a critical dimension ($d_{critical}$).

In the exemplary embodiment of FIG. 3B, apertures 325B include two apertures having a semi-circular shape. In the exemplary embodiment of FIG. 3C, apertures 325C include two apertures having a half ring or arcuate shape.

Figure 4:
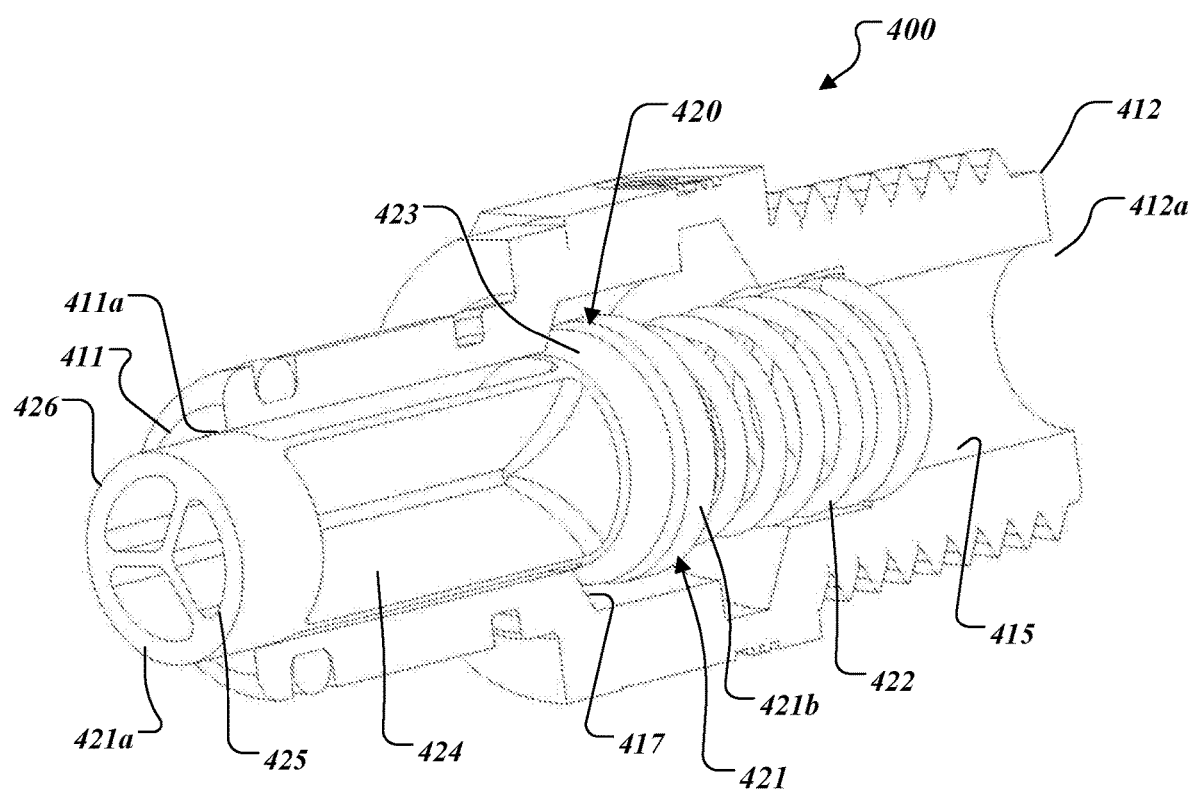
FIG. 4 shows a partial cross-sectional view of an exemplary coupling body member having a male first end.

Referring to FIG. 4, an exemplary male coupling body member 400 is shown including apertures 425 with a size, shape and configuration to provide desirable flow characteristics while reducing spillage of retained fluid in the internal volume of male coupling body member 400. Similar to coupling body member 100 described herein, male coupling body member 400 includes an interior space defined by inner sidewall 415 between first and second ends 411, 412. First and second ends 411, 412 include first and second ports 411a, 412a, respectively, and are connectable to a fluid source, outlet or other suitable component, such as female coupling body member 100, so that the interior space defines a passage through which fluid may flow between first and second ends 411, 412.

In an exemplary embodiment, a second valve assembly 420 is disposed within the interior space and is configured to be translatable between an open position and a closed position to selectively allow fluid flow through male coupling body member 400. Second valve assembly 420 may be similar to first valve assembly 120 and includes a second closure member 421, a biasing member 422, and a seal 423 (e.g., o-ring) that sealingly engages with a valve seat 417. Second closure member 421 includes a forward end 421a, a rear end 421b, and an elongate portion 424 extending between forward and rear ends 421a, 421b. In an exemplary embodiment, a piston head 426 is positioned proximate forward end 421a and defines one or more apertures 425 extending longitudinally through a thickness of piston head 426. Seal 423 is positioned proximate rear end 421b and spaced from piston head 426. In an exemplary embodiment, rear end 421b is a solid end without openings or passages extending through, such that fluid may only flow through male coupling body member 400 by passing between rear end 421b and inner sidewall 415.

Apertures 425 allow fluid to flow through interior space of male coupling body member 400 when valve assembly 420 is in an open configuration. In an exemplary embodiment, apertures 425 of male coupling body member 400 may have any suitable size, shape and configuration as described herein, for example as described in connection with apertures 125, to avoid excessive flow restriction while preventing or reducing the potential for spillage of fluid that may be present in an internal volume ($V_{internal}$) of male coupling body member 400.

Figure 5:
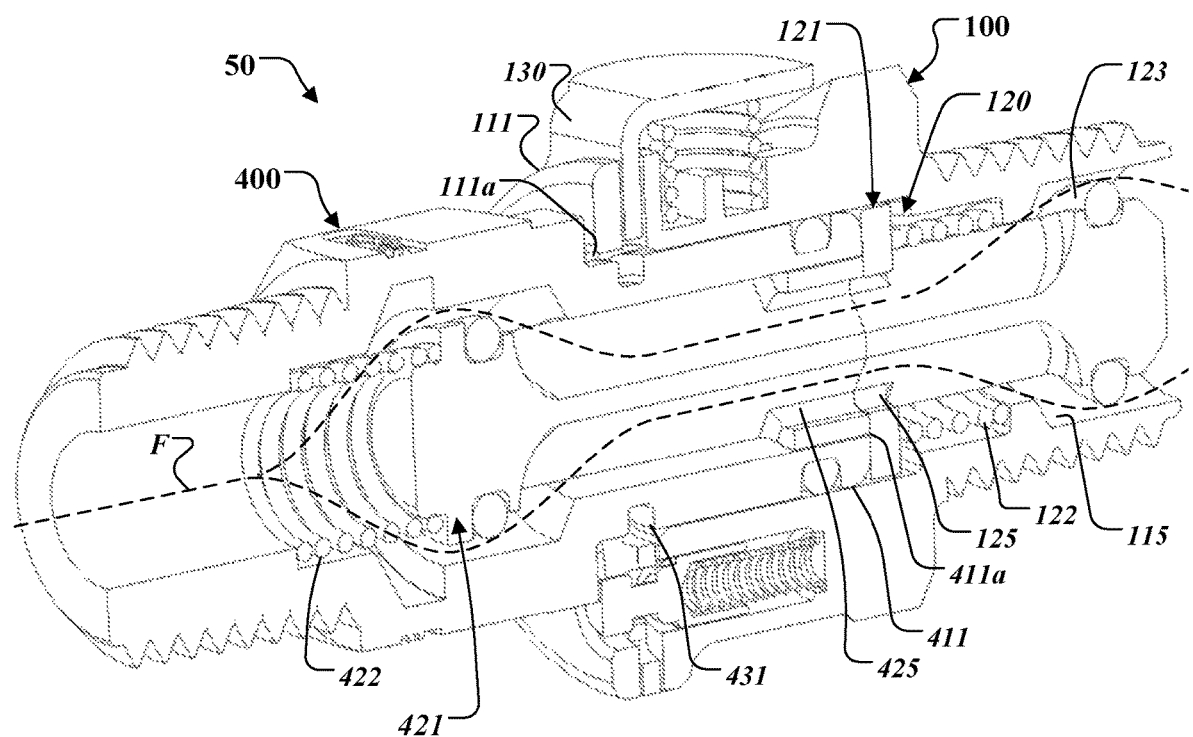
FIG. 5 shows a perspective cross-sectional view of exemplary coupling body members in a connected configuration.

Referring to FIG. 5, an exemplary embodiment of a fluid coupling device 50 is shown including a female coupling body member 100 having a female first end 111 connected to male first end 411 of male coupling body member 400. Male first end 411 is received by first port 111a such that female coupling body member 100 and male coupling body member 400 may be sealingly joined.

Female and male coupling body members 100, 400 include one or more complementary attachment features. In an exemplary embodiment, female coupling body member 100 includes a spring-loaded latch 130 that interacts with a complementary feature of male coupling body member 400, such as a groove 431. Such features allow secure engagement between respective first ends 111, 411 of female and male coupling body members 100, 400, while facilitating rapid connection and/or disconnection by axial movement. In some exemplary embodiments, female and male coupling body members 100, 400 may be quickly joined without requiring rotational movement. In other exemplary embodiments, female and male coupling body members 100, 400 may connected by any suitable feature or technique that provides a secure connection, including a threaded connection, bayonet connection, snap connection, relative rotation, or interference connection.

Closure member 421 and/or one or more other components of male coupling body member 400 interacts with first valve assembly 120 to compress biasing member 122 and move sealing surface 123 away from inner surface 115 and into an open position. Similarly, closure member 121 and/or one or more other components of coupling body member 100 interacts with closure member 421 to compress biasing member 422, moving seal 423 away from inner surface 415 and into an open position. When female coupling body member 100 is connected to male coupling body member 400, first and second valve assemblies are in an open position, and inner sidewalls 115, 415 of female and male coupling body members 100, 400 define a flow passage (F) between second end port 112a through first end ports 111a, 411a, and out second end port 412a.

In various exemplary embodiments, apertures 425 are similar or identical to apertures of a component to which male coupling body member 400 is connectable with, such as apertures 125 of a coupling body member 100. For example, apertures 125 and apertures 425 may have a nearly identical size, shape and configuration such that apertures 425 may be aligned with apertures 125 when male coupling body member 400 is joined with a female coupling body member. Alternatively or additionally, apertures 425 may include one or more apertures having a size, shape or configuration that differs from apertures 125 of a female coupling body member, and in some embodiments, male coupling body member 400 may be used independently of female coupling body member 100 or another component having such apertures. In various exemplary embodiments, apertures 425 have a maximum major dimension ($d2_{aperture}$) between distant sides of each aperture 425. Maximum major dimension ($d2_{aperture}$) may be sized as described herein with respect to apertures 125 to be less than a critical dimension ($d_{critical}$), and within one or more ranges described herein, for example. Similarly, apertures 425 may include two or more apertures having a total open cross-sectional area ($A2_{apertures}$) having a desired relationship with one or more other components or dimensions of male coupling body member 400, as described herein with respect to female coupling body member 100.

To disconnect female and male coupling body members 100, 400, the process may be reversed, causing closure members 121, 421 to return to a closed position. For example, spring-loaded latch 130 may be manually depressed such that complementary features of female and male coupling body members 100, 400 are disengaged, and the components separated by moving laterally away from one another. In various exemplary embodiments, fluid may be retained in internal volumes ($V_{internal}$) between apertures 125, 425 and seals 123, 423, respectively. As described herein, apertures 125, 425 may prevent, or at least inhibit, fluid in respective internal volumes ($V_{internal}$) from escaping, reducing or preventing dripping or spillage from female and male coupling body members 100, 400 that may otherwise occur.

Figure 6:
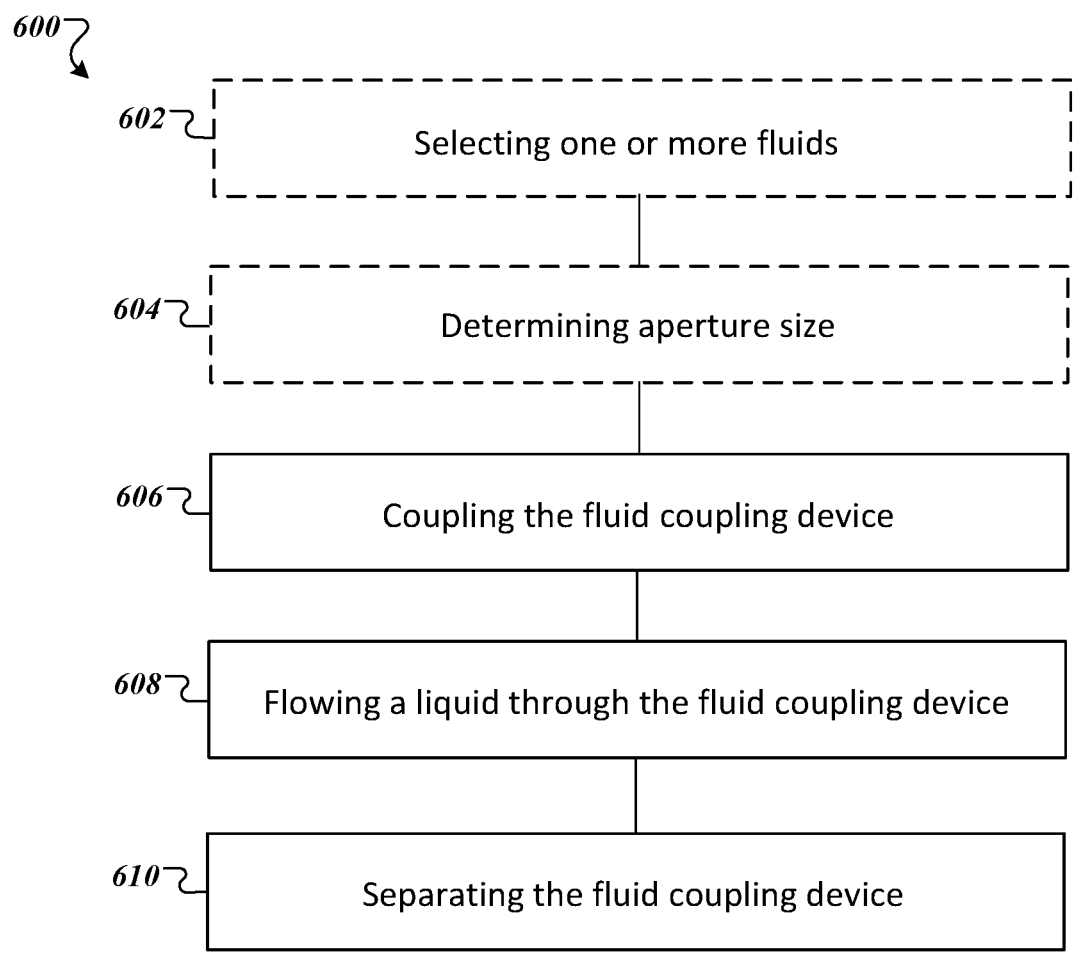
FIG. 6 shows a flow diagram of an exemplary method of using a fluid coupling device.

Referring to FIG. 6, a flow diagram of an exemplary method 600 for using a fluid coupling device is shown. While the depicted example pertains to a fluid coupling device, it should be understood that the anti-spillage concepts described herein can be implemented in other fluid handling component contexts such as, but not limited to, dip tubes, drop tubes, nipples, nozzles, tubes, pipes, valves, fittings, and the like. In an exemplary embodiment, method 600 may optionally include operation 602 of selecting one or more fluids to be used with the fluid coupling device. The fluid may include any number of fluids that may pass through fluid coupling device in use, and in some exemplary embodiments, may include one or more of water, glycerol, ethylene glycol, isopropyl alcohol, perfluoro ether oil, and/or other fluids.

Exemplary method 600 may also include optional operation 604 of determining a type of piston head aperture(s) of the fluid coupling device based on both surface tension and density of a fluid. In some exemplary embodiments, operation 604 includes determining a critical acceleration according to the equations provided below.

In various exemplary embodiments, method 600 includes operation 606 of coupling the fluid coupling device. For example, the fluid coupling device may be coupled with a component of fluid dispensing equipment, hose, tube, container, valve, fitting or other connector. The fluid coupling device includes one or more apertures that define a critical acceleration that is at or above a target value. The apertures and other components of the fluid coupling device may be manufactured to have any features and dimensional relationships described herein.

Method 600 may further include operation 608 of flowing one or more fluids through the fluid coupling device. In some exemplary embodiments, the fluids passing through the fluid coupling device exhibit a surface tension and density such that the critical acceleration of the fluid coupling device is greater than or equal to a target value.

At operation 610, the fluid coupling device may be separated from a complementary coupler or other fluid component such that fluid present in the fluid coupling device is retained rather than spilling out of an open end through the apertures. In some exemplary embodiments, separating the fluid coupling device results in more than 25%, more than 50%, more than 75%, more than 85%, more than 95% or approximately 100% of fluid present in internal volume ($V_{internal}$) being retained within the fluid coupling device.

In various exemplary embodiments, apertures as described herein may be included in any fluid component or coupling device to prevent or reduce spillage from an internal volume. Apertures may be defined by a component of a valve assembly, such as a movable closure member 121 or a stationary component proximate an open end, for example. In some exemplary embodiments, apertures may be present in an independent fluid component that is not coupled with another component during normal use, such as a free end of a hose or a dip tube.

EXPERIMENTS and EXAMPLES

Introduction: In many industrial processes, it is desirable to prevent liquid from spilling or draining from tubes, pipes or various other de-coupled fluid handling components. In practical use, most fluid-handling components may be subjected to accelerations due to being jolted, impacted, and/or shaken. Therefore, a method is needed to quantify the non-spill characteristics of a component exposed to the accelerations associated with jolting, impacting, shaking, and the like. To do so, experiments were performed to model fluid-handling components having one open end. The fluid-handling components were filled with liquid and attached to a spinning apparatus. The component was rotated at progressively higher rates to initiate spillage and drainage. The angular velocity was recorded when the liquid spillage initiated. Critical acceleration values ("critical acceleration" as used herein is the acceleration at which spillage initiates for a particular design) were calculated. The critical acceleration is indicative of the acceleration at which spillage initiates regardless of the cause of the acceleration (e.g., spinning {such as spinning performed during these experiments}, other types of movements, impacts, jolts, and the like). It was found that critical acceleration values were independent of radial distance from the center of rotation, yet they were dependent on factors such as, but not limited to, wetting properties between solid-liquid interfaces. The critical acceleration is also dependent on parameters such as, but not limited to, contact angles, and tube diameter as well as surface tension, and density. The results obtained from these experiments are in well agreement with the model predictions. Experimental results are compared to models that assume that onset of drainage is determined by an interplay of surface and body forces.

Figure 7:
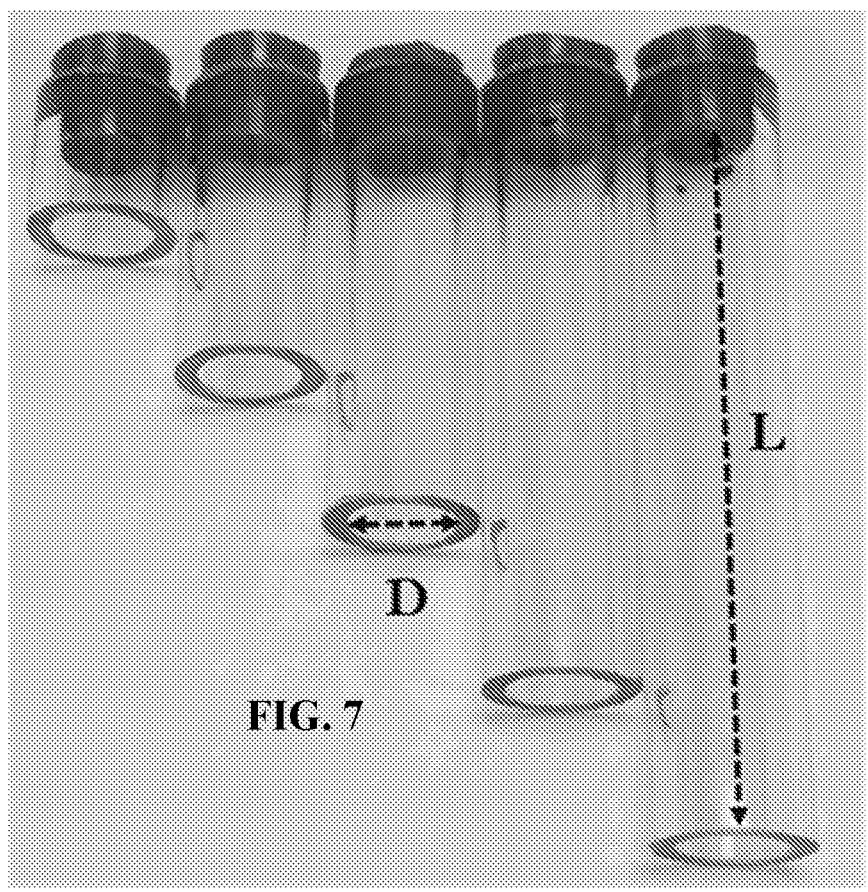
FIG. 7 shows a perspective view of a group of tubes having equal diameters and differing lengths.
Figure 8:
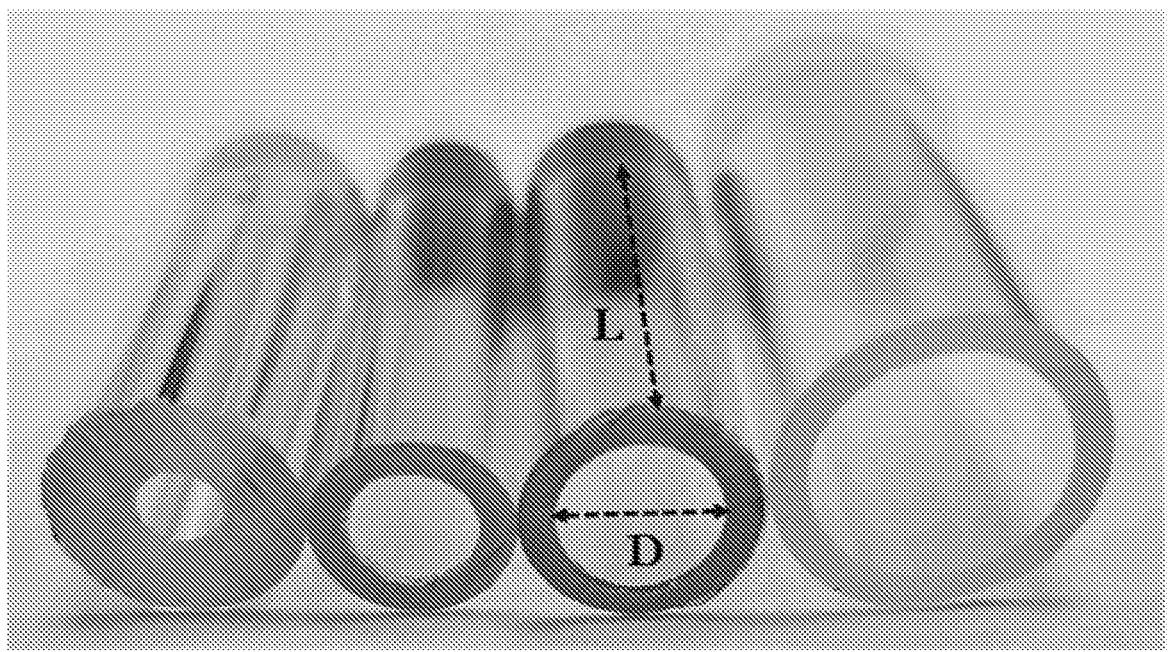
FIG. 8 shows a perspective view of a group of tubes having equal lengths and differing diameters.

Background:

For simplicity, components can be modeled as a cylindrical tube. Examples of some of the tubes used during this experimentation are shown in FIGS. 7 and 8. One end of the tubes was closed and sealed. Tube lengths L experimented with were 0.5 cm, 1.5 cm, 2.5 cm, 3.5 cm, and 4.5 cm (from left to right in FIG. 7). The other end of each of the tubes in FIG. 7 have a circular opening of diameter D (0.64 cm in this case). All tubes in FIG. 7 are made of polycarbonate.

Tubes of various diameters, as shown in FIG. 8, were also experimented with. The tube diameters D tested were 0.32 cm, 0.48 cm, 0.64 cm, and 0.95 cm (from left to right in FIG. 8). All tubes in FIG. 8 are polycarbonate and have the identical lengths L of 2.5 cm.

The tubes were filled with a liquid that has surface tension of $\gamma$ and density of $\rho$. The tube's material of construction (polycarbonate in this case) exhibits advancing and receding contact angles of $\theta_a$ and $\theta_r$. The tube is oriented horizontally. If its diameter D is sufficiently small, liquid will not drain.

Figure 9:
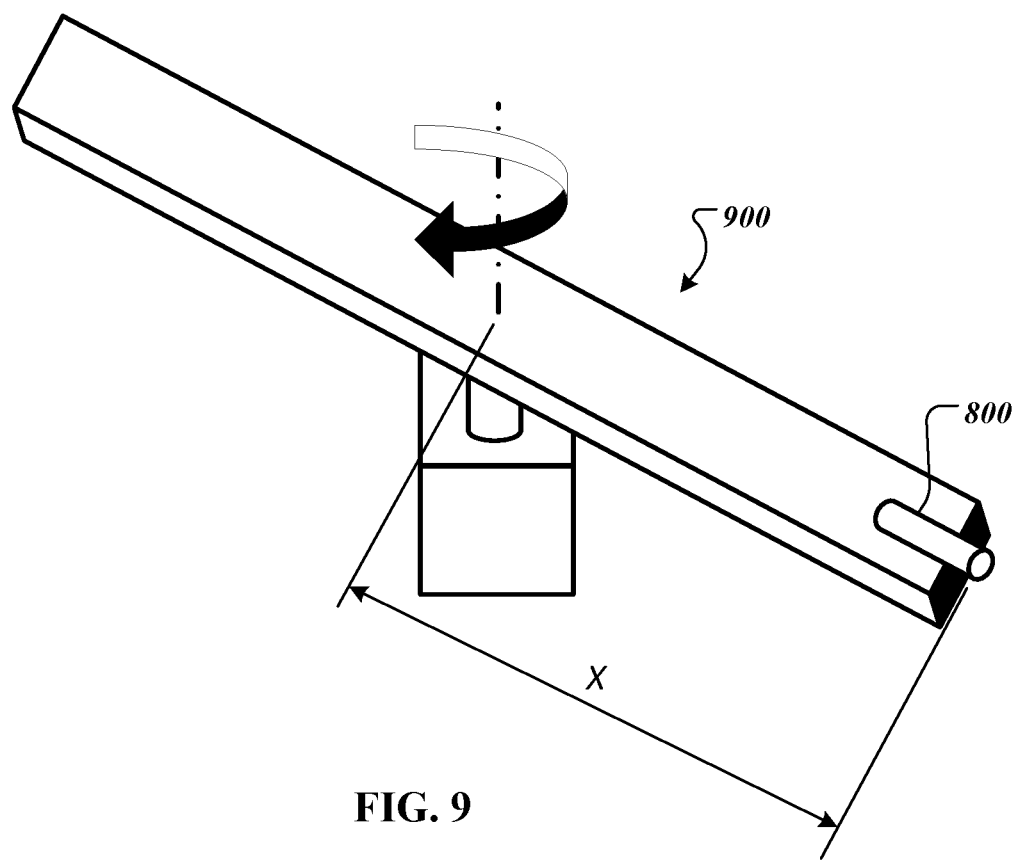
FIG. 9 shows a perspective view of a test device for measuring the acceleration at which liquid spills from a tube with a single open end.

As depicted in FIG. 9, a tube 800 was attached to the arm of a spinning apparatus 900. The open end of the tube 800 is facing outward, such the distance from the spindle to the open end of the tube is x. The tube 800 is spun at a progressively higher angular velocity ($\omega$) that creates an acceleration (a) at the end of the open tube 800, wherein:

$$a = \omega^2 x. \quad \text{(Equation 2)}$$

As the acceleration increases, liquid at the open end of the tube 800 will distort as shown in FIGS. 10 and 11. The convex bulge on the bottom portion of the liquid to air interface and concave dimple of the top portion of the liquid to air interface become more pronounced with increasing angular velocities. If a critical acceleration ($a_c$) is exceeded, then liquid will drain from the spinning tube 800.

The critical acceleration to initiate flow ($a_c$) can be estimated by equating the opposing body and surface pressures acting on the protruding lower bulge, $$\Delta p_b = \Delta p_s. \quad \text{(Equation 3)}$$

If the shape of lower bulge at the critical acceleration is assumed to be a hemi-ellipsoid, the critical body pressure ($\Delta p_b$) can be estimated as $$\Delta p_b = \rho V a / A, \quad \text{(Equation 4)}$$

where V and A are the volume and cross-sectional area of the lower bulge, $$V = \frac{2\pi}{3} R_1^2 R_2, \quad \text{(Equation 5)}$$

$$A = \pi R_1 R_2, \quad \text{(Equation 6)}$$

and $R_1$ and $R_2$ are its principal radii. The curvature of the bulge along with the surface tension of the liquid creates a surface or Laplace pressure ($\Delta p_s$) that counteracts the body pressure, $$\Delta p_s = \frac{\gamma}{R_1} + \frac{\gamma}{R_2}. \quad \text{(Equation 7)}$$

The wettability of the tubes affects the shape of the bulge. Two scenarios are considered (FIGS. 10 and 11). In the first scenario, the advancing contact angle ($\theta_a$) is large ($\theta_a \gg 0°$) and the lower bulge is pinned at the inner edge of the tube as depicted in FIG. 10. The receding contact angle ($\theta_r$) can be any value $\theta_r \geq 0°$. Here, for a round aperture, the principal radii of curvature are approximated as:

$$R_1 = \frac{1}{3 + \cos\theta_r} D \quad \text{(Equation 8)}$$

and $$R_2 = \left[\frac{1}{4} - \left(\frac{1}{2} - \frac{1}{3 + \cos\theta_r}\right)^2\right]^{1/2} D. \quad \text{(Equation 9)}$$

Combining Equations (3) through (9) yields the following estimate of the critical acceleration ($a_c$) required to dislodge liquids from tubes where $\theta_a \gg 0°$ and $\theta_r \geq 0°$, $$a_c = \frac{3}{2}(3 + \cos\theta_r) \quad \text{(Equation 10)}$$

$$\left\{3 + \cos\theta_r + \left[\frac{1}{4} - \left(\frac{1}{2} - \frac{1}{3 + \cos\theta_r}\right)^2\right]^{-1/2}\right\} \frac{\gamma}{\rho D^2}.$$

If $\theta_r = 0°$, then Equation 10 reduces to $$a_c = 24(1 + 3^{-1/2}) \frac{\gamma}{\rho D^2}. \quad \text{(Equation 11)}$$

In the second scenario, the tubing is essentially completely wetted by the liquid ($\theta_a = \theta_r = 0°$) and the lower bulge will be pinned at the outer edge of the tubing as shown in FIG. 11. The principal radii of curvature can be approximated as $$R_1 = \frac{D + B}{4} \quad \text{(Equation 12)}$$

and $$R_2 = \frac{1}{2}\left[D^2 - \frac{1}{4}(D - B)^2\right]^{1/2}. \quad \text{(Equation 13)}$$

where B is the wall thickness of a tube.

Combining equations (3)-(7), (12) and (13) yields an equation for estimating the critical acceleration ($a_c$) required to dislodge liquids from wettable tubes where $\theta_a = \theta_r = 0°$, $$a_c = \frac{12\gamma}{\rho(D+B)}\left[\frac{2}{D+B} + \left[D^2 - \frac{1}{4}(D-B)^2\right]^{-1/2}\right].$$ (Equation 14)

Figure 26:
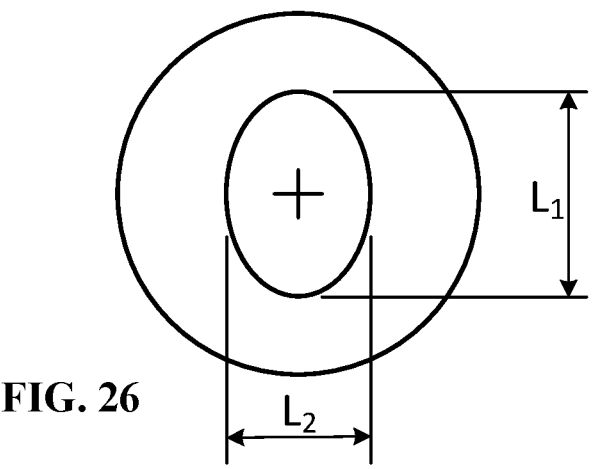
FIGS. 26-28 are end views of example fluid handling components that include non-circular openings.
Figure 27:
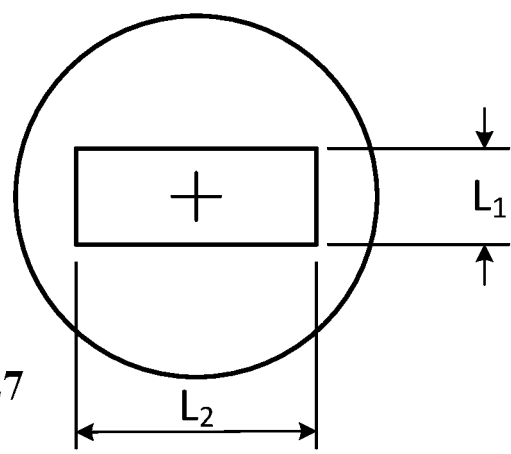
Figure 28:
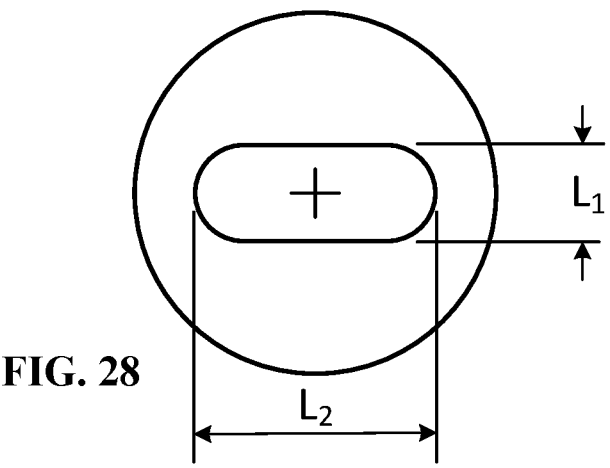

Following the same type of analysis as detailed above, for a tube made of a hydrophobic material (e.g., where $\theta_a \gg 0°$ and $\theta_r \geq 0°$), and for a single opening that is any shape (including non-circular shapes such as rectangular, ovular, triangular, square, etc.), the critical acceleration ($a_c$) required to dislodge liquid from the tube is $$a_c = \frac{2\gamma A}{\rho V}\left[\frac{2}{L_1} + \frac{1}{L_2}\right]$$ (Equation 15)

where V and A are the volume and cross-sectional area of the lower bulge (refer to FIG. 10 for an example of a lower bulge in a tube made of hydrophobic material), $L_1$ is the vertical height of the opening, and $L_2$ is the horizontal width of the opening. FIG. 26, for example, illustrates a single elliptical opening with a vertical height of $L_1$ and a horizontal width of $L_2$ as shown. FIG. 27 provides another example of single non-circular opening—in this case a single rectangle with a vertical height of $L_1$ and a horizontal width of $L_2$ as shown. For additional understanding, FIG. 28 illustrates another exemplary single non-circular opening—in this case an ovular shape with a vertical height of $L_1$ and a horizontal width of $L_2$ as shown. The critical acceleration ($a_c$) required to dislodge liquid through the openings of the tubes shown in FIGS. 26-28 is defined by Equation 15 (assuming the tubes are made of a hydrophobic material).

Figure 29:
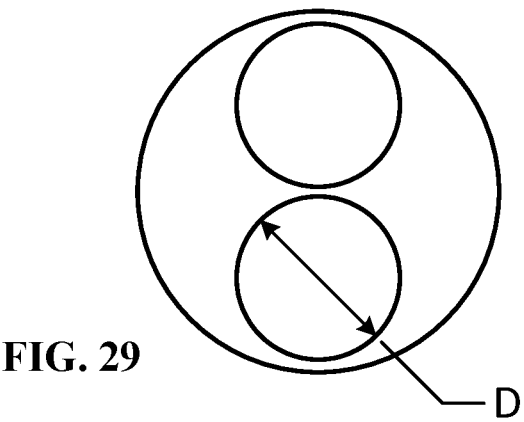
FIGS. 29-31 are end views of example fluid handling components that include multiple circular openings.
Figure 30:
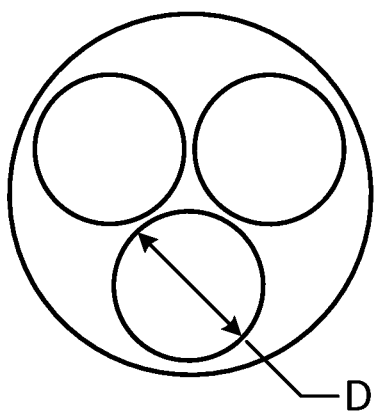
Figure 31:
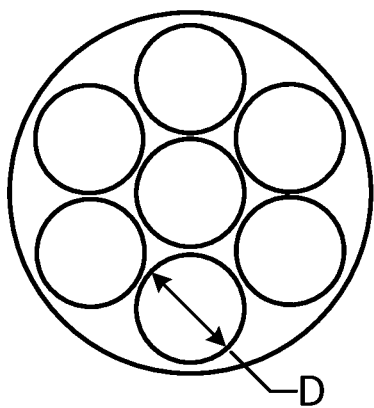

Referring to FIGS. 29-31, when a tube made of hydrophobic material has multiple circular openings of the same size (diameter=D), liquid is likely to exit through just one of the openings (despite having multiple openings). The critical acceleration ($a_c$) required to dislodge liquid from the tube (through the single opening) is $$a_c = \frac{12\gamma}{\rho D^2}.$$ (Equation 16)

When a tube made of hydrophobic material has multiple openings of any shape (including non-circular shapes such as rectangular, ovular, triangular, square, etc.) that are the same size, liquid is likely to exit through just one of the openings (despite having multiple openings). The critical acceleration ($a_c$) required to dislodge liquid from the tube is $$a_c = \frac{2\gamma A}{\rho V}\left[\frac{1}{L_1} + \frac{1}{L_2}\right]$$ (Equation 17)

where $L_1$ is the vertical height of the opening, and $L_2$ is the horizontal width of the opening.

Figure 32:
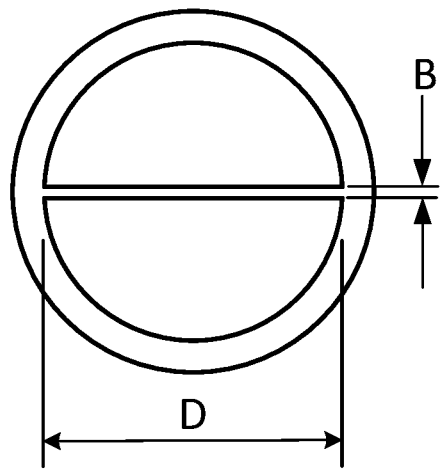
FIG. 32 is an end view of an example fluid handling component having a two-vane design.

Referring to FIG. 32, when a tube made of hydrophobic material has a two-vane design, the critical acceleration ($a_c$) at which liquid will dislodge from the tube through one of the openings is $$a_c = \frac{36\gamma}{\rho D^2}.$$ (Equation 18)

Figure 33:
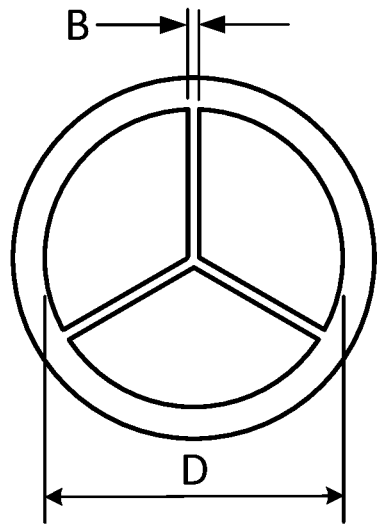
FIG. 33 is an end view of an example fluid handling component having a three-vane design.
Figure 34:
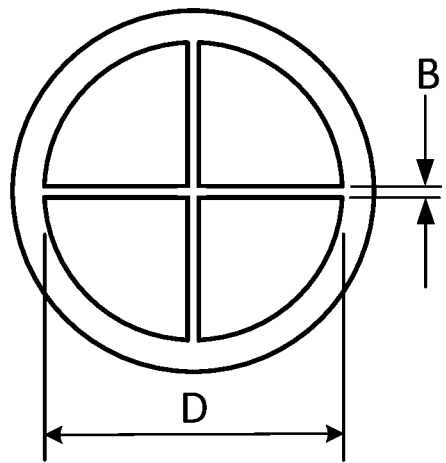
FIG. 34 is an end view of an example fluid handling component having a four-vane design.
Figure 35:
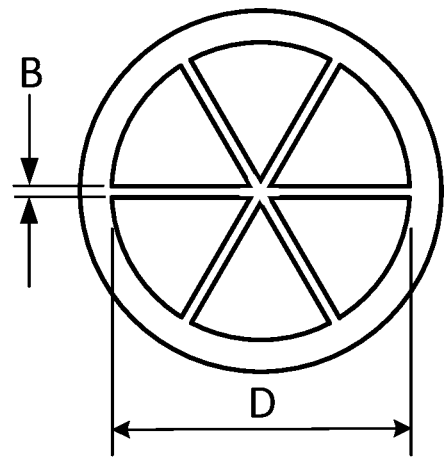
FIG. 35 is an end view of an example fluid handling component having a six-vane design.

Referring to FIGS. 33-35, when a tube made of hydrophobic material has a multiple-vane design, the critical acceleration ($a_c$) at which liquid will dislodge from the tube through one of the openings is $$a_c = \frac{6}{n}\frac{1}{(D/2)\text{Sin}(180°/n) - B}$$
$$\left[\frac{1}{D/4 - B/2} + \frac{1}{(D/2)\text{Sin}(180°/n) - B}\right]\frac{\gamma}{\rho}$$ (Equation 19)

where n is the number of openings and B is the vane thickness. For example, still referring to the multiple-vane designs of FIGS. 33-35, if for the sake of illustration we assume D is equal to 5.5 mm and B is equal to 0.66 mm, the critical accelerations ($a_c$) at which liquid will dislodge from the tubes through one of the openings are as follows: (i) $a_c$=78.4 m/sec² for the three vane design of FIG. 33, (ii) $a_c$=89.18 m/sec² for the four vane design of FIG. 34, and (iii) $a_c$=147.0 m/sec² for the six vane design of FIG. 35.

Experimental Details:

The liquids used were deionized (DI) water, ethanol (Sigma Aldrich, >99.5%, CAS 64-17-5), and ethylene glycol (Fisher BioReagents, ≥99%, CAS 107-21-1. Density ($\rho$) of the liquids, taken from the literature, are 998 kg/m³, 789 kg/m³, and 1110 kg/m³, respectively. Uncertainty of $\gamma$ and $\rho$ was estimated to be ±1 mN/m and ±2 kg/m³.

Cylindrical polymeric tubes of various types were purchased from McMaster-Carr; polycarbonate (PC, #8585K), acetal (POM, #8627K), polyvinyldene fluoride (PVDF, #51105K), nylon 6,6 (PA, #8628K), high-density polyethylene (HDPE, #50375K), Teflon (PTFE, #8547K), and perfluoroalkoxy alkane (PFA, #52705K). Tubes were cut at desired lengths to obtain the tubes shown in FIGS. 7 and 8. Uncertainty in diameters (D) was estimated to be ≤±0.1 mm.

An auto tensiometer (Kyowa DyneMaster DY-300) was used to measure the surface tension of liquids ($\gamma$). Liquids were filled into clean glass dishes designated for the tensiometer. Prior to each measurement a platinum Wilhelmy plate was cleaned in alcohol flame. During the measurements, the platinum plate was automatically dipped in the liquid and the surface tension value was displayed on the DYNALYZER software in mN/m (or dyne/cm).

Advancing and receding contact angles were measured using a digital goniometer (Kyowa DropMaster DMs-401). To measure an advancing contact angle ($\theta_a$), a sessile water drop was initially deposited on the cylindrical tubes (appx. 7 μl). Then the drop volume was increased using a syringe dispenser. To measure a receding contact angle ($\theta_r$), water was withdrawn from a sessile drop until the contact line retracted. With the needle of the syringe still contacting the drop, an image was captured. Base and tangent lines were constructed on the various drop images, then $\theta_a$ and $\theta_r$ were measured directly. Advancing and receding contact angles ($\theta_a$ and $\theta_r$) of the various liquid-solid combinations are listed in Table 2 below. Values of $\theta_a$ and $\theta_r$ were ranged from 6° to 112°. Standard deviation and uncertainty in the contact angle measurements was generally ±3°.

Apart from the tube composition evaluation, polycarbonate (PC) tubes were used for spin experiments due to their rigidity and transparency. For simplicity, all numerical results collected from the spin experiments are plotted against critical acceleration divided by gravitational acceleration, critical acceleration ratio ($a_c/g$). During the spin experiments, cylindrical tubes were filled with liquid. The tubes 800 were placed on the stage of the spinning apparatus 900 and oriented horizontally with open-end facing outward as depicted in FIG. 9. The stage was spun with constant acceleration using a frequency controller. The instant that the liquid spilled out of the tubes 800, the frequency was recorded. Frequencies were later converted to an acceleration value using Equation 2. Slow motion recordings and all related images were captured. All experiments were performed three times at 23±2° C. Averages and standard deviations were computed.

Results and Discussion:

The experiments determined which parameters are significant in terms of initiation of drainage behavior from cylindrical tubes including the fluid handling components and their designs. Parameters studied in these experiments included tube position from the center of rotation, tube length, tube diameters, wall thickness, tube composition/wettability, and liquid type/surface tension. Points in the graphs (e.g., FIGS. 12-15, 17, and 19) represent experimental data, and lines represent prediction using the equations in the theory section.

A tube position experiment was conducted to determine whether the critical acceleration ($a_c$) varies with distance (x) as depicted in FIG. 9. The tubes were tested at several distances from the center of rotation. Maximum distance ($x_{max}$) was 15 cm, and minimum distance ($x_{min}$) was 3 cm. According to the results displayed in FIG. 12, the critical acceleration ratio does not significantly change with varying tube positions. The small variation is considered to be within the experimental uncertainty.

Figure 13:
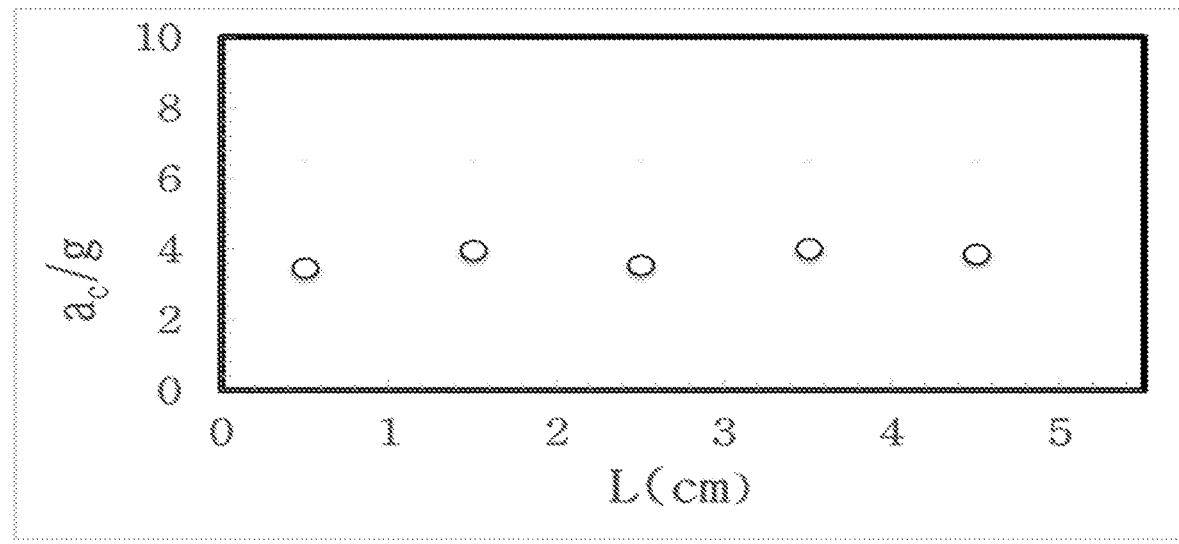
FIG. 13 is a graph of the critical accelerations (when liquid spillage occurred) of tubes having various lengths (with consistent diameters and wall thicknesses).
Figure 14:
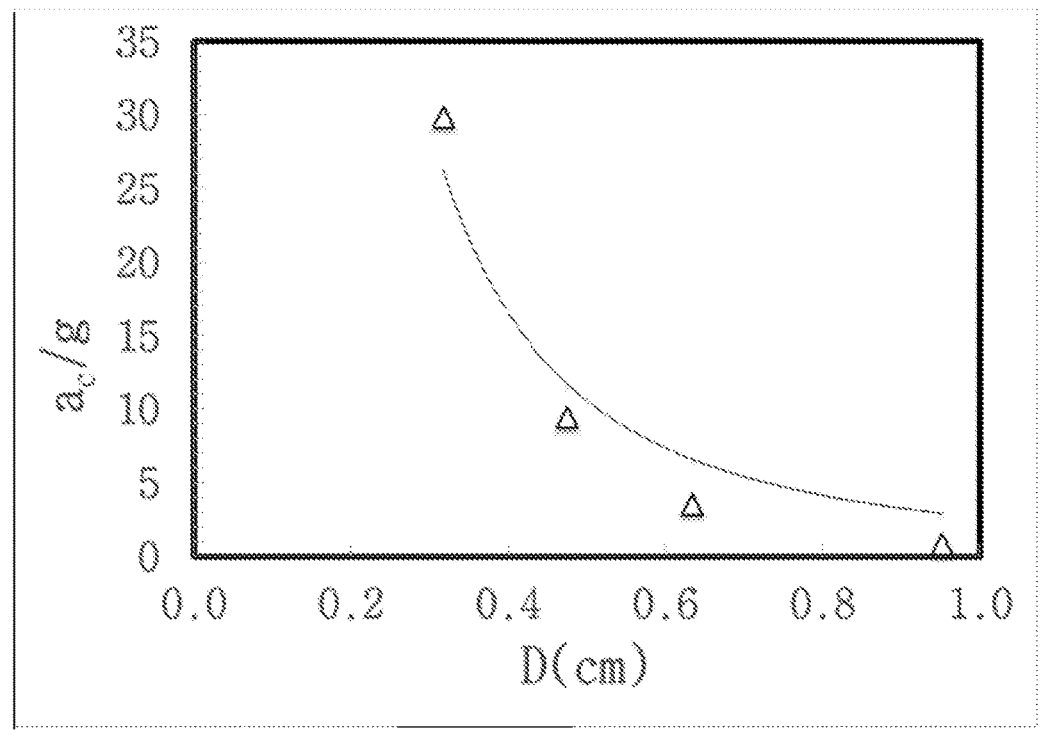
FIG. 14 is a graph of the critical accelerations (when liquid spillage occurred) of tubes having various diameters (with consistent wall thicknesses and lengths).

To investigate tube length, the five tubes shown in FIG. 7 were used. The diameter and the wall thicknesses of the tubes were kept constant. There was no significant critical acceleration ratio change observed at different tube lengths as depicted in FIG. 13.

FIG. 8 shows the PC tubes that were used to investigate tube diameter. All the tubes have the same length of 2.5 cm. The tube with 0.32 cm diameter has a different wall thickness from other tubes, yet wall thickness parameter is ineffectual when deionized water is used as the liquid (shown later in the report). The critical acceleration ratio drastically decreases with increasing tube diameter, shown in FIG. 14. This variation is also predicted by Equation 10 where $a_c$ is inversely proportional to the square of diameter.

The effect of the tube construction material is shown in Table 1. Considering the wetting influence, the spillage behavior largely depends on the receding contact angle (see Table 2) of liquid on polymeric tubes. If tubes have high receding contact angles (e.g., PFA, PTFE), water spills at lower critical accelerations. On the contrary, water spills at higher critical accelerations from tubes (e.g., PC, PVDF) due to the low receding contact angles. If the receding contact angle is non-zero, and the advancing contact angle is much bigger than zero, the critical acceleration will be affected by a receding contact angle changed as shown in Equation 10.

TABLE 1

| Tube Composition | $a_c/g$ Experimental | Calculated |
|---|---|---|
| PC | 28.9 ± 1.4 | 26.3 |
| PVDF | 30.3 ± 1.5 | 26.2 |
| PA | 25.8 ± 0.8 | 26.9 |
| POM | 28.9 ± 1.4 | 23.3 |
| HOPE | 19.6 ± 1.8 | 20.9 |

TABLE 1-continued

| Tube Composition | $a_c/g$ Experimental | Calculated |
|---|---|---|
| PFA | 13.8 ± 0.8 | 18.3 |
| PTFE | 13.7 ± 0.5 | 18.6 |

TABLE 2

| Cylindrical tubes | DI water (W) $\theta_a$ | DI water (W) $\theta_r$ | Ethylene glycol (EG) $\theta_a$ | Ethylene glycol (EG) $\theta_r$ | Ethanol (E) $\theta_a$ | Ethanol (E) $\theta_r$ |
|---|---|---|---|---|---|---|
| PC | 105° | 29° | 53° | 10° | 13° | 6° |
| PVDF | 104° | 30° | | | | |
| PA | 101° | 23° | | | | |
| POM | 98° | 52° | | | | |
| HDPE | 108° | 67° | | | | |
| PFA | 108° | 82° | | | | |
| PTFE | 112° | 80° | | | | |
| PP | 106° | 84° | | | | |
| WS | 99° | 33° | | | | |

Figure 15:
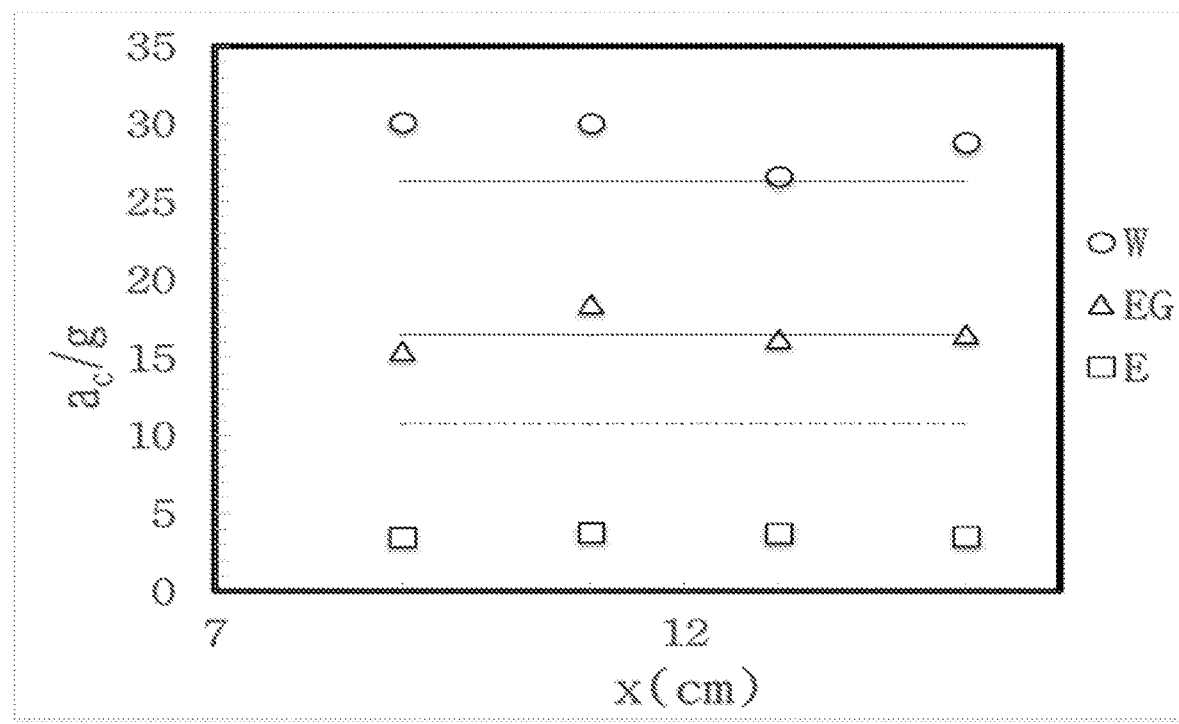
FIG. 15 is a graph of the critical accelerations (when liquid spillage occurred) of tubes containing water, ethylene glycol, and ethanol (with consistent lengths, diameters, and wall thicknesses).

The most common fluid used in many industrial applications is water, and its surface tension is ~72 mN/m in room temperature. Another common fluid is ethanol which represents a lower surface tension liquid, at ~22 mN/m. Ethylene glycol exhibits a surface tension of ~48 mN/m, which lies in between water and ethanol. FIG. 15 clearly indicates the effect of liquid surface tension, where lower surface tension causes spillage at much lower critical acceleration ratios. The theoretical prediction for water (W) and ethylene glycol (EG) agrees with the experimental data, yet the ethanol (E) data is in disagreement. Since ethanol completely wets most surfaces, the first model presented in equation is not representative of the scenario due to being valid at higher advancing contact angles. There, the wall thickness which is discussed next was also investigated.

Figure 16:
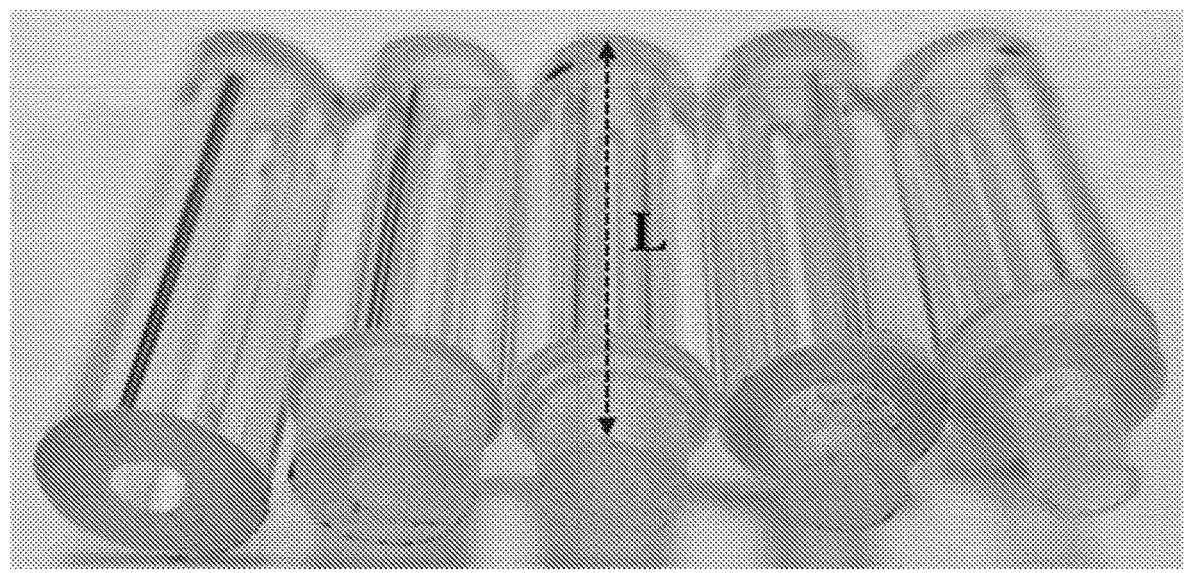
FIG. 16 shows a perspective view of a group of tubes having equal lengths, equal inner diameters, and differing wall thicknesses (at the end portions of the tubes).
Figure 17:
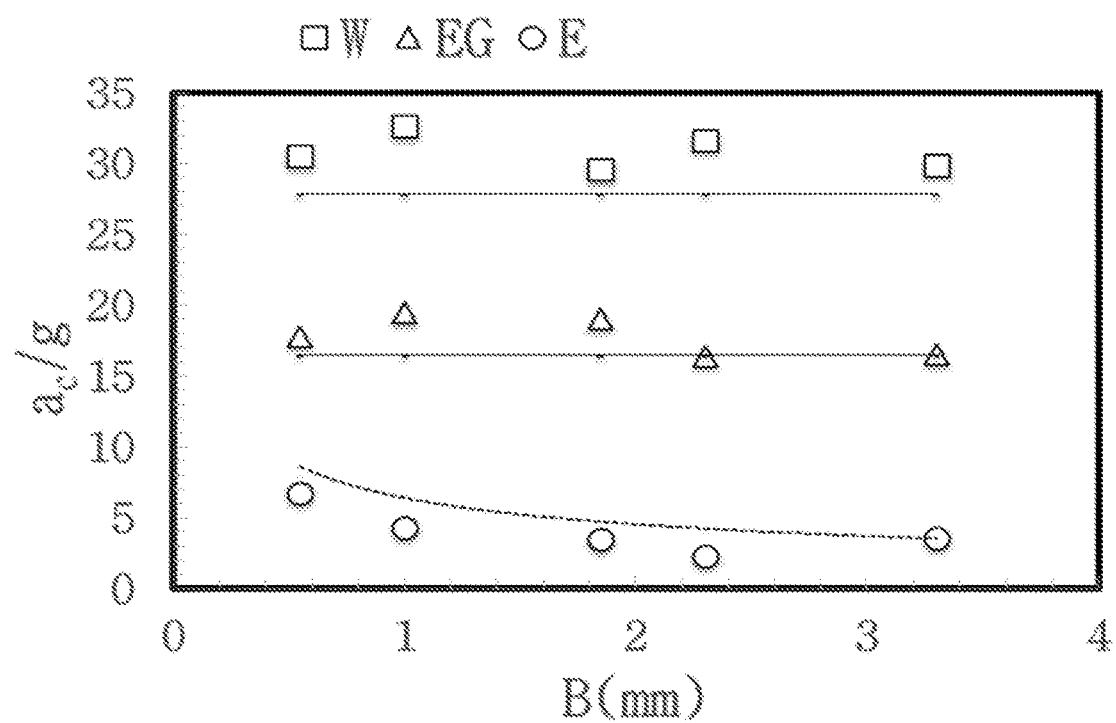
FIG. 17 is a graph of the critical accelerations (when liquid spillage occurred) of the tubes of FIG. 16 containing water, ethylene glycol, and ethanol.

It was hypothesized that ethanol was wetting the walls of the tubes. To test this, PC tubes were machined down to reduce their outer diameter (OD), keeping the inner diameter (ID) constant, shown in FIG. 16. FIG. 17 exhibits experimental results from the PC tubes with different wall thicknesses. Water (W) and ethylene glycol (EG) were constant in $a_c/g$, whereas ethanol (E) shows an increase as the wall thickness decreases. The scenario of ethanol is modeled and shown using Equation 14.

Figure 18:
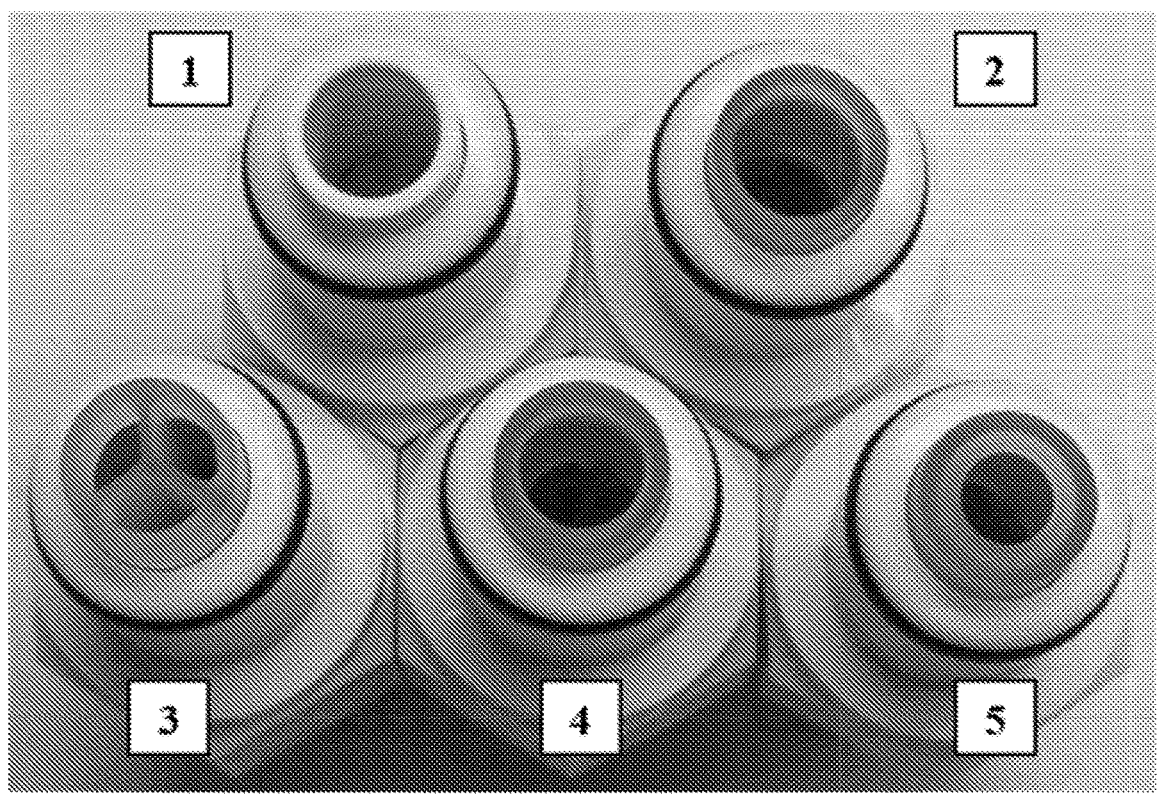
FIG. 18 is a photo showing fluid coupling devices with five different types of valve apertures.
Figure 19:
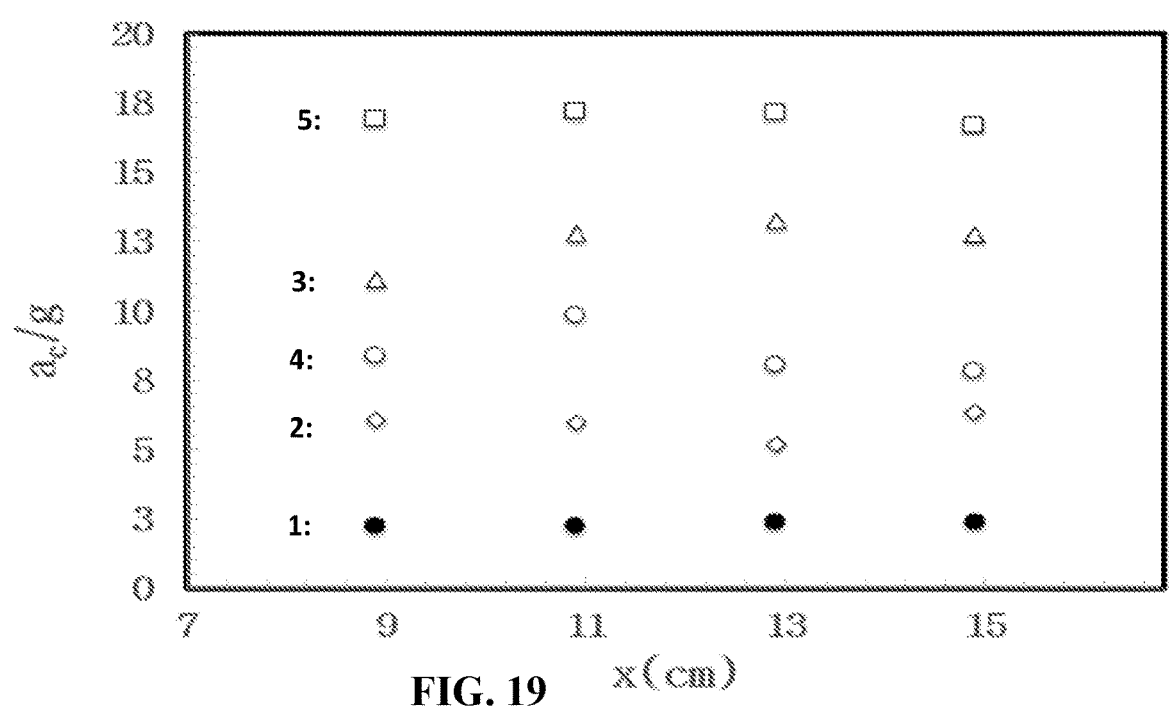
FIG. 19 is a graph comparing the critical accelerations (when liquid spillage occurred) of the fluid coupling devices of FIG. 18.

The fluid coupling devices shown in FIG. 18 were tested using DI water. Results are displayed in FIG. 19. As expected, the component #1 spilled at a lower critical acceleration than other components. The critical acceleration of component #2 is slightly higher than #1 due the lower receding angle of watershed (WS) material (3D printed with Somos WaterShed XC 11122). Component #3 and #4 showed higher critical acceleration values than the first two, and they are very close to each other. Component #5 has shown the highest critical acceleration value among all the components, approximately five times more than the traditional valve in component #1. Equation 10 was used to estimate the critical acceleration ratios for the valves with a single round orifice (i.e., 1, 2, 4 and 5). For the three-vane design (#3), if we assume the $\theta_a$=90°, then the critical acceleration can be estimated as $$a_c = \frac{3}{2}\frac{\gamma}{\rho g R_1}\left(\frac{1}{R_1} + \frac{1}{R_2}\right), \quad \text{(Equation 20)}$$

where the radii of curvature in the lower of the three holes were measured to be $R_1$=1.2 mm (the distance across the opening along a line that bisects the obtuse angle, from the obtuse angle to the wall opposite of the obtuse angle) and $R_2$=1.8 mm (the distance across the opening between the opposing acute angles), respectively. The predicted values, shown in Table 3, generally agreed with the experimental values. Equation 10 over-predicted g values for the largest openings (#1 & #2). This is attributed to their relatively low resistance to drainage that allowed some of the water to spill during disconnect and handling (tubes or couplers that are partially full exhibit less resistance to spillage than full ones).

TABLE 3

| Component # | a_c/g | |
| --- | --- | --- |
| | Experimental | Calculated |
| 1 | 2.3 ± 0.1 | 5.9 |
| 2 | 5.9 ± 0.4 | 8.5 |
| 3 | 12.5 ± 0.8 | 12.9 |
| 4 | 8.5 ± 0.8 | 10.4 |
| 5 | 17.0 ± 0.2 | 19.0 |

CONCLUSIONS

The experiments evaluated the drainage behavior due to spinning using polymeric cylindrical tubes and liquids. The critical acceleration for spillage from tubes depends on wettability of tube material, tube diameter, and surface tension of liquids introduced. The wall thickness may have an effect if a liquid with low surface tension (e.g., ethanol) is used. Two models to explain spillage have been derived. The first model exhibits a scenario where critical acceleration depends on receding contact angle and the tube diameter. The spillage behavior of water and ethylene glycol can be explained with the first model. This model could also be reduced to a simpler equation if the receding contact angle was zero. The second model includes the wall thickness parameter which can be used to explain the spillage behavior of ethanol. In this case the advancing and receding contact angles are nearly zero. In both scenarios, the critical acceleration is directly proportional to liquid surface tension and inversely proportional to liquid density. The fluid handling components with newly designed valves (as described further below) exhibited higher critical acceleration results. A small design addition to fluid coupling devices with traditional valves can potentially make a big impact in terms of lowering or stopping drainage/spillage in many applications.

The principles derived from the aforementioned experimentation can be used to design fluid coupling devices that advantageously inhibit or eliminate liquid spillage associated with the disconnection of two previously-mated fluid couplings. That is, the inventors have confirmed that fluid coupling devices can be designed to inhibit or eliminate spillage through an orifice(s) using design concepts such as, but not limited to: (i) reducing the size (e.g., diameter) of the orifice(s), (ii) reducing the thickness of the wall that defines the orifice(s), and (iii) increasing the wettability of the material that defines the orifice(s). Such design principles have been put to practical use in the following structures.

Figure 20:
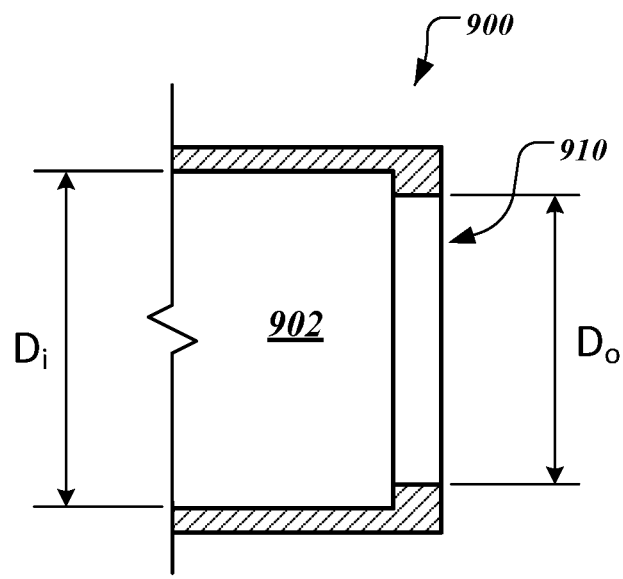
FIG. 20 is a longitudinal cross-sectional view of a type of aperture that is designed to increase the critical acceleration.

Referring to FIG. 20, an example fluid coupling device 900 (partially shown, and shown in longitudinal cross-section) defines an internal volume 902. The internal volume 902 has an inclusion diameter $D_i$. The internal volume 902 is open to ambient at an orifice 910.

In this example embodiment, the orifice 910 is defined by an annular, inwardly-projecting lip that defines an orifice diameter $D_o$. In some cases, more than one orifice 910 can be included in a single fluid coupling device 900. The fluid coupling device 900 can be representative of a piston head of a female fluid coupling device (e.g., first coupling body member 20 as shown in FIG. 1B) and/or of a male fluid coupling device (e.g., second coupling body member 30 as shown in FIG. 1C). While in the depicted embodiment the orifice is circular, one of ordinary skill in the art will recognize that the inventive concepts disclosed herein also pertain to non-circular orifices such as, but not limited to, ovular, triangular, polygonal, and the like.

In the depicted example of fluid coupling device 900, orifice diameter $D_o$ is smaller than inclusion diameter $D_i$. Accordingly, the tendency of fluid coupling device 900 to spill liquid from the internal volume 902 is reduced because of the reduced size of orifice diameter $D_o$ (in comparison to the larger inclusion diameter $D_o$. More particularly, the critical acceleration $a_c$ associated with liquid contained in the internal volume 902 of the fluid coupling device 900 is increased because of the reduced size of orifice diameter $D_o$ (compared to the larger inclusion diameter $D_i$). Accordingly, the fluid coupling device 900 is less apt to spill liquid when two previously-mated fluid couplings are disconnected.

As described above, for hydrophobic materials the critical acceleration $a_c$ of fluid coupling device 900 can be expressed by Equation 11:

$$a_c = 24(1 + 3^{-1/2})\frac{\gamma}{\rho D o^2}.$$

Equation 11 shows an inverse relationship between the orifice diameter $D_o$ and the critical acceleration $a_c$ for hydrophobic materials. Accordingly, as the orifice diameter $D_o$ is decreased, the critical acceleration $a_c$ is increased. Because of that, the use of the annular, radially-inward-projecting lip that defines an orifice diameter $D_o$ beneficially makes the fluid coupling device 900 more resistant to spillage.

Figure 21:
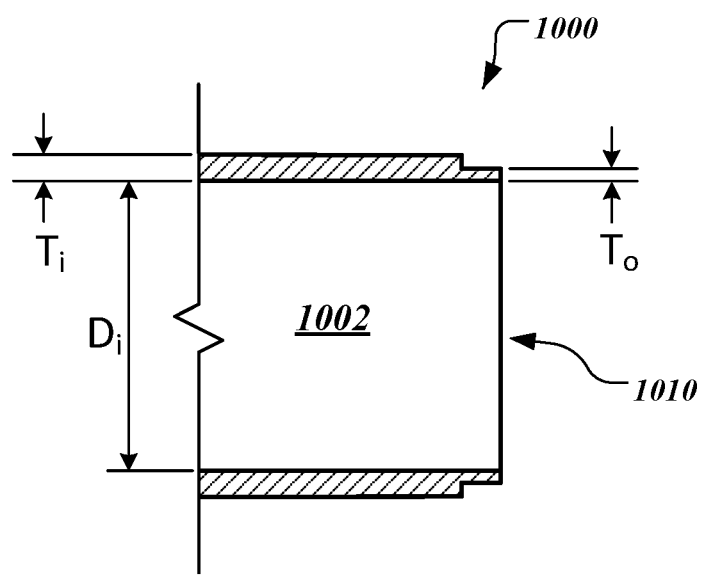
FIG. 21 is a longitudinal cross-sectional view of another type of aperture that is designed to increase the critical acceleration.

Referring to FIG. 21, an example fluid coupling device 1000 (partially shown, and shown in longitudinal cross-section) defines an internal volume 1002. The internal volume 1002 has an inclusion diameter $D_i$. The internal volume 1002 is open to ambient at an orifice 1010. In this example, the diameter defined by the orifice 1010 is equal to the inclusion diameter $D_i$.

In this example embodiment, the orifice 1010 is defined by a peripheral wall having a wall thickness $T_o$. Other portions of the internal volume 1002 have a peripheral wall with a wall thickness $T_i$. The wall thickness $T_o$ is thinner than the wall thickness $T_i$. Accordingly, for at least some liquids, the tendency of fluid coupling device 1000 to spill liquid from the internal volume 1002 is reduced because of the reduced wall thickness $T_o$ at the orifice 1010 (in comparison to the wall thickness $T_i$). More particularly, the critical acceleration $a_c$ associated with liquid contained in the internal volume 1002 of the fluid coupling device 1000 is increased because of the reduced wall thickness $T_o$ at the orifice 1010 (compared to the thicker wall Ti). This is true (at least for some liquids) even though the inclusion diameter $D_i$ is the same at the orifice 1010 as the inclusion diameter $D_i$ at internal portions of the space that defines the internal volume 1002. Accordingly, because of the reduced wall thickness $T_o$ at the orifice 1010, the fluid coupling device 1000 is less apt to spill liquid when two previously-mated fluid couplings are disconnected.

As described above, the critical acceleration $a_c$ of fluid coupling device 1000 can be expressed by the Equation 10:

$$a_c = \frac{3}{2}(3+\cos\theta_r)\left\{3+\cos\theta_r+\left[\frac{1}{4}-\left(\frac{1}{2}-\frac{1}{3+\cos\theta_r}\right)^2\right]^{-1/2}\right\}\frac{\gamma}{\rho D^2}$$

In some cases, more than one orifice 1010 can be included in a single fluid coupling device 1000. The fluid coupling device 1000 can be representative of a piston head of a female fluid coupling device (e.g., first coupling body member 20 as shown in FIG. 1B) and/or of a male fluid coupling device (e.g., second coupling body member 30 as shown in FIG. 1C).

Figure 22:
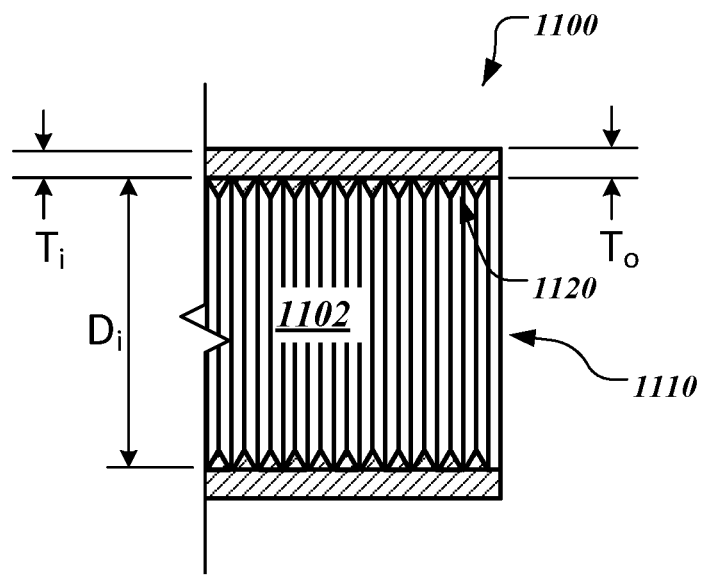
FIG. 22 is a longitudinal cross-sectional view of another type of aperture that is designed to increase the critical acceleration.

Referring to FIG. 22, an example fluid coupling device 1100 (partially shown, and shown in longitudinal cross-section) defines an internal volume 1102. The internal volume 1102 has an inclusion diameter $D_i$. The internal volume 1102 is open to ambient at an orifice 1110. In this example, the diameter defined by the orifice 1010 is equal to the inclusion diameter $D_i$. The wall thickness $T_i$ of the internal volume 1002 is similarly consistent throughout.

In this example embodiment, the inner wall surface that defines the internal volume 1102 has been made rougher as schematically represented by a grooves in the wall surface 1120. Such a roughened wall surface 1120 is one way to increase the wettability of the material that defines the internal volume 1102. Additional ways to increase the wettability of the material that defines the internal volume 1102 can include, but are not limited to, using surface treatments and/or coatings, or choosing a material with a higher surface energy, to provide a few examples. As described above, an increase in the wettability of the material that defines the internal volume 1102 will cause an increase in the critical acceleration $a_c$ associated with liquid contained in the internal volume 1102 of the fluid coupling device 1100. Accordingly, because of the increased roughness of the inner wall surface that defines the internal volume 1102, the fluid coupling device 1100 is less apt to spill liquid when two previously-mated fluid couplings are disconnected.

As described above, for hydrophobic materials the critical acceleration $a_c$ of fluid coupling device 1100 can be expressed by Equation 11:

$$a_c = 24(1+3^{-1/2})\frac{\gamma}{\rho D^2}.$$

The fluid coupling device 1100 can be representative of a piston head of a female fluid coupling device (e.g., first coupling body member 20 as shown in FIG. 1B) and/or of a male fluid coupling device (e.g., second coupling body member 30 as shown in FIG. 1C).

Figure 23:
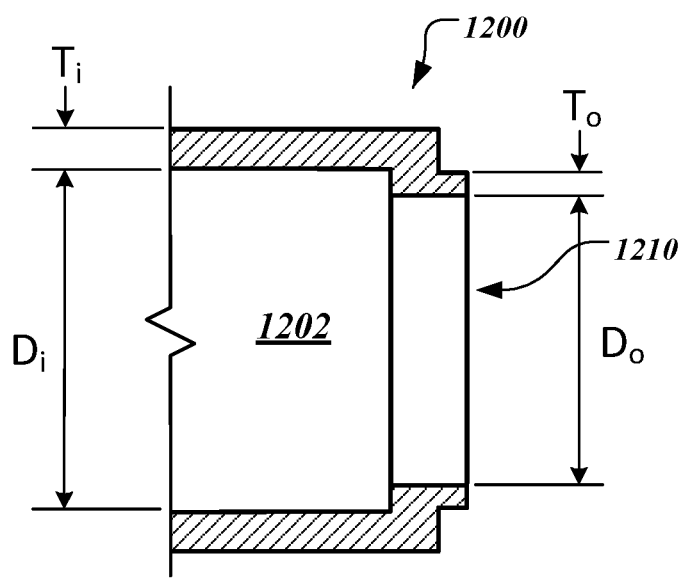
FIG. 23 is a longitudinal cross-sectional view of another type of aperture that is designed to increase the critical acceleration.

It should be understood that the design principles described in the context of FIGS. 20-22 can be combined in any desired manner, and all such combinations and permutations are within the scope of this disclosure. For example, referring to FIG. 23, the example fluid coupling device 1200 (partially shown, and shown in longitudinal cross-section) defines an internal volume 1202 and an orifice 1210. The orifice 1210 is defined by an annular lip that defines a diameter $D_o$ that is smaller than the diameter $D_i$ of the more-interior portions of the internal volume 1202. In addition, the orifice 1210 is defined by a peripheral wall with a wall thickness $T_o$ that is thinner than the more-interior portions of the internal volume 1202 that have a wall thickness $T_i$. In this example, the reduced diameter of the orifice 1210 and the reduced wall thickness at the orifice 1210 function in concert to make the fluid coupling device 1200 less apt to spill liquid when two previously-mated fluid couplings are disconnected.

As described above, for hydrophobic materials the critical acceleration $a_c$ of fluid coupling device 1200 can be expressed by Equation 11:

$$a_c = 24(1+3^{-1/2})\frac{\gamma}{\rho Do^2}.$$

Figure 24:
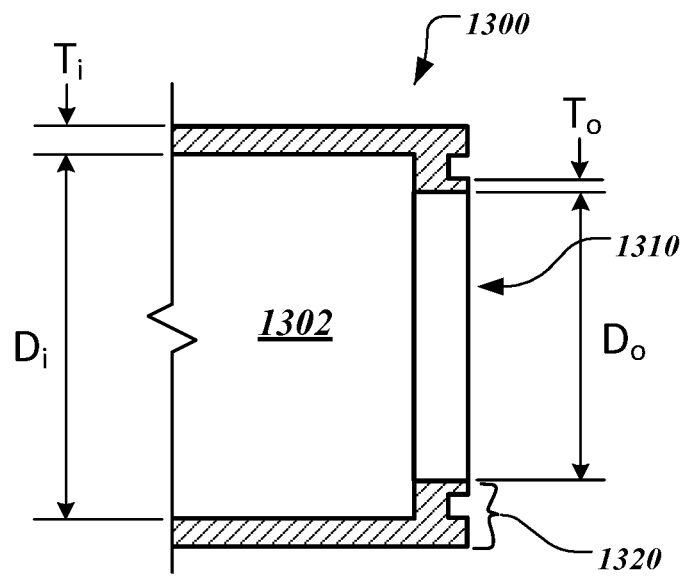
FIG. 24 is a longitudinal cross-sectional view of another type of aperture that is designed to increase the critical acceleration.

Referring to FIG. 24, the example fluid coupling device 1300 (partially shown, and shown in longitudinal cross-section) defines an internal volume 1302 and an orifice 1310. The orifice 1310 is defined by an annular lip that defines a diameter $D_o$ that is smaller than a diameter $D_i$ of the more-interior portions of the internal volume 1302. In addition, the orifice 1310 is defined by a peripheral wall with a wall thickness $T_o$ that is thinner than the more-interior portions of the internal volume 1302 that have a wall thickness $T_i$. In this example, the reduced diameter of the orifice 1310 and the reduced wall thickness at the orifice 1310 function in concert to make the fluid coupling device 1300 less apt to spill liquid when two previously-mated fluid couplings are disconnected.

In the depicted embodiment, the thinner wall thickness $T_o$ of the fluid coupling device 1300 is protected from damage by being set back towards the more-interior portions of the internal volume 1302. That is, fluid coupling device 1300 includes a face 1320 that is defined by the thinner wall thickness $T_o$ and by the thicker wall thickness $T_i$. In some embodiments, the thinner wall thickness $T_o$ of the fluid coupling device 1300 is protected from damage by being set back even farther towards the more-interior portions of the internal volume 1302 (such that only the thicker wall thickness $T_i$ defines the face 1320).

As described above, for hydrophobic materials the critical acceleration $a_c$ of fluid coupling device 1300 can be expressed by Equation 11:

$$a_c = 24(1+3^{-1/2})\frac{\gamma}{\rho Do^2}.$$

Figure 25:
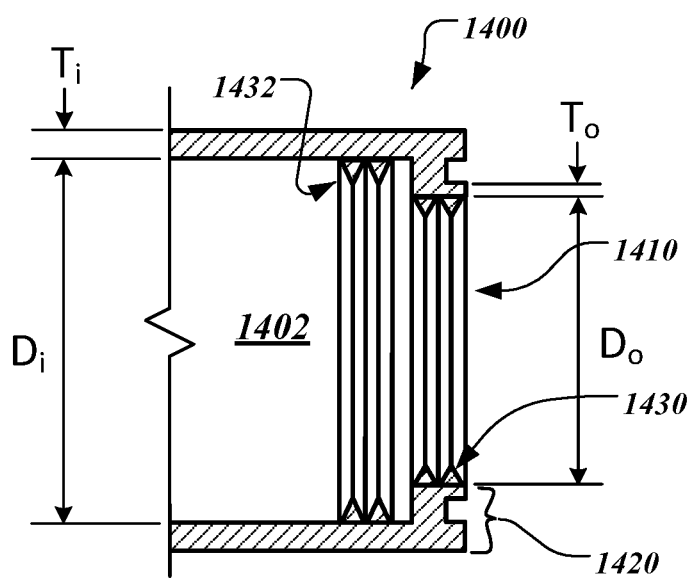
FIG. 25 is a longitudinal cross-sectional view of another type of aperture that is designed to increase the critical acceleration.

Referring to FIG. 25, the example fluid coupling device 1400 (partially shown, and shown in longitudinal cross-section) defines an internal volume 1402, a face 1420, and an orifice 1410. The orifice 1410 is defined by an annular lip that defines a diameter $D_o$ that is smaller than a diameter $D_i$ of the more-interior portions of the internal volume 1402. The orifice 1410 is defined by a peripheral wall with a wall thickness $T_o$ that is thinner than the more-interior portions of the internal volume 1402 that have a wall thickness $T_o$. In addition, at least some portions of the wall surface(s) that define internal volume 1402 include roughened areas 1430, 1432 to increase the wettability of the material that defines the internal volume 1402. In this example, the reduced diameter of the orifice 1410, the reduced wall thickness at the orifice 1410, and the increased wettability of the internal volume 1402 resulting from the roughened areas 1430, 1432 all function in concert to make the fluid coupling device 1400 less apt to spill liquid when two previously-mated fluid couplings are disconnected.

As described above, for hydrophobic materials the critical acceleration $a_c$ of fluid coupling device 1400 can be expressed by Equation 11:

$$a_c = 24(1+3^{-1/2})\frac{\gamma}{\rho Do^2}.$$

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Although a number of implementations have been described in detail above, other modifications are possible. For example, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. An anti-spillage poppet valve fluid coupling device, comprising:
a first coupling body member configured to mate with a second coupling body member and defining a longitudinal axis and an interior space defined by an inner sidewall between a first port and an opposing second port; and
a first poppet valve assembly disposed at least partially within the interior space, the first poppet valve assembly comprising:
a first closure member having: (i) a forward end region, (ii) a rear end region, (iii) a piston head proximate the forward end region and (iv) a sealing surface proximate the rear end region, the first closure member longitudinally movable within the interior space between: (a) a closed position in which the sealing surface prevents fluid communication between the first port and the second port, and (b) an open position in which the first port and the second port are in fluid communication,
the piston head having a circular outer circumference,
the piston head defining two or more apertures extending longitudinally through the piston head, and
wherein a face of the piston head defines grooves such that each of the two or more apertures is surrounded by a groove.

2. The anti-spillage poppet valve fluid coupling device of claim 1, wherein each of the two or more apertures are partially defined by an annular lip that projects radially inward.

3. The anti-spillage poppet valve fluid coupling device of claim 1, wherein wall surfaces defining each of the two or more apertures are textured, thereby increasing a wettability of the wall surfaces defining the two or more apertures.

4. The anti-spillage poppet valve fluid coupling device of claim 1, wherein the two or more apertures comprise at least two apertures.

5. The anti-spillage poppet valve fluid coupling device of claim 1, wherein the two or more apertures comprise at least three apertures.

6. The anti-spillage poppet valve fluid coupling device of claim 1, wherein at least one of the two or more apertures is circular.

7. The anti-spillage poppet valve fluid coupling device of claim 1, wherein at least one of the two or more apertures is generally triangular.

8. The anti-spillage poppet valve fluid coupling device of claim 1, wherein the two or more apertures includes three generally triangular apertures.

\* \* \* \* \*